(12) United States Patent
Shao et al.

(10) Patent No.: US 6,410,920 B1
(45) Date of Patent: *Jun. 25, 2002

(54) METHOD AND APPARATUS FOR PERFORMING CORRECTION OF EMISSION CONTAMINATION AND DEADTIME LOSS IN A MEDICAL IMAGING SYSTEM

(75) Inventors: Lingxiong Shao, San Jose, CA (US); Hugo Bertelsen, Aalborg (DK); Peter Nelleman, Pleasanton; Horace Hines, San Jose, both of CA (US)

(73) Assignee: ADAC Laboratories, Milpitas, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/400,745

(22) Filed: Sep. 21, 1999

Related U.S. Application Data

(63) Continuation-in-part of application No. 08/865,930, filed on May 30, 1997, now Pat. No. 6,008,493.

(51) Int. Cl.$^7$ .............................................. G01T 1/164
(52) U.S. Cl. .................................................. 250/363.04
(58) Field of Search ..................... 250/363.03, 363.04, 250/363.07, 363.09; 378/7

(56) References Cited

U.S. PATENT DOCUMENTS

| | | |
|---|---|---|
| 3,745,345 A | 7/1973 | Muehllehner |
| 4,424,446 A | 1/1984 | Inbar et al. |
| 4,588,897 A | 5/1986 | Inbar et al. |
| 4,599,690 A | 7/1986 | Stoub |
| 5,296,708 A | 3/1994 | Moyers et al. |
| 5,444,252 A | 8/1995 | Hug et al. |
| 5,461,232 A | 10/1995 | McCandless et al. |
| 5,471,061 A | 11/1995 | Moyers et al. |

(List continued on next page.)

OTHER PUBLICATIONS

Siu K. Yu and Claude Nahmias, "Single Photon Transmission Measurements In Positron Tomography Using $^{137}$Cs," McMaster University Medical Centre, Hamilton, Ontario, 1995, pp. 1–29.

Karp, et al., "Singles Transmission In Positron Emission Tomography Using $^{137}$Cs," IEEE Nuclear Science Symposium and Medical Imaging Conference record vol. 13, 1995, pp. 1363–1367.

(List continued on next page.)

*Primary Examiner*—Constantine Hannaher
(74) *Attorney, Agent, or Firm*—Eugene E. Clair

(57) ABSTRACT

A method of correcting for deadtime and for emission contamination of a transmission scan in a nuclear camera system is provided. The transmission scan is used to correct positron emission tomography (PET) images for attenuation. The camera system includes two detectors and two corresponding single-photon point sources that are collimated to produce fanbeam illumination profiles. A transmission detection window and an emission contamination detection window is defined on each detector. Radiation from each source is scanned axially across the field of view of the corresponding detector in synchronization with the corresponding transmission detection window to acquire transmission projection data. The emission contamination detection windows are also scanned axially concurrently with, but offset from, the transmission detection windows to acquire emission data. Events detected in the transmission detection windows are used to add counts from appropriate locations of the transmission projection on an event-by-event basis in real-time. Events detected in the emission contamination detection windows are used to subtract counts from appropriate locations of the transmission projection on an event-by-event basis as those events are detected. The number of counts by which a given location is incremented or decremented for each detected event is determined event-by-event from a look-up table based on the current singles rate.

58 Claims, 21 Drawing Sheets

U.S. PATENT DOCUMENTS

| | | |
|---|---|---|
| 5,552,606 A | 9/1996 | Jones et al. |
| 5,585,637 A | 12/1996 | Bertelsen et al. |
| 5,596,197 A | 1/1997 | Jones et al. |
| 5,600,145 A | 2/1997 | Plummer |
| 5,608,221 A | 3/1997 | Bertelsen et al. |
| 5,742,056 A | 4/1998 | Valentino et al. |
| 6,008,493 A | * 12/1999 | Shao et al. ............ 250/363.04 |

OTHER PUBLICATIONS

P. Nellemann, et al., "Performance Characteristics of a Dual Head SPECT Scanner with PET Capability," IEEE Nuclear Science Symposium and Medical Imaging Conference Record, vol. 3, 1995, pp. 1751–1755.

Karp, et al., "Singles Transmission in Volume–Imaging PET with a $^{137}$Cs Source," *Phys. Med. Biol.,* vol. 40, 1995, pp. 929–944.

R.A. De Kemp, et al., "Design and Performance of 3D Photon Transmission Measurement on a Positron Tomograph with Continuoulsy Rotating Detectors," Interanational Meeting on Fully Three–Dimensional Image Reconstructuion in Radiology and Nuclear Medicine, 1995, pp. 51–54.

James A. Sorenson, Ph.D. et al., *Physics in Nuclear Medicine,* 2nd Ed., W.B. Saunders Company, Philadelphia, 1987, pp. 252–259, 443, 451.

R.J. Smith and J.S. Karp, "Simultaneous Post–Injection Transmission and Emission Contamination Scans in a Volume Imaging PET Scanner," IEEE Nuclear Science Symposium and Medical Imaging Conference Records, vol. 3, 1995, pp. 1781–1785.

Robert Anthony Dekemp, B.A.Sc., "Attenuation Correction in Positron Emission Tomography Using Single Photon Transmission Measurement," Sep. 1992, 106 pages.

Bailey, et al., "ECAT ART—A Continuously Rotating PET Camera: Performance Characteristics, Initial Clinical Studies, and Installation Considerations in a Nuclear Medicine Department," European Journal of Nuclear Medicine, vol. 24, No. 1, Jan. 1997, 10pages.

G. Muehllehner, et al., "Performance Paramters of a Positron Imaging Camera," IEEE Transactions on Nuclear Science, vol. NS–23, No. 1, Feb. 1976, pp. 528–537.

Gerd Muehllehner, "Positron Camera with Extended Counting Rate Capability," Journal of Nuclear Medicine, vol. 16, No. 7, Jul. 1975, pp. 653–657.

Karp, et al., "Continous–Slice PENN–PET: A Positron Tomograph with Volume Imaging Capability," Journal of Nuclear Medicine, vol. 31, No. 5, May 1990, pp. 617–627.

R.J. Smith, et al., "Singles Transmission Scans Performed Post–Injection for Quantitative Whole Body PET Imaging," IEEE Nuclear Science Symposium Conference Record, vol. 3, Nov. 1996, 7 pages.

Karp, et al., "Attenuation Correction in PET Using a Singles Transmission Source," Abstract No. 156 From Proceedings of the 41$^{st}$ Annual Meeting, Scientific Papers, vol. 35, No. 5, May 1994, p. 41P.

G. Muehllehner, et al., "Spect Scanner with PET Coincidence Capability," Abstract No. 284, From Proceedings of the 42$^{nd}$ Annual Meeting, Scientific Papers, Journal of Nuclear Medicine, Jun. 14, 1995, p. 70P.

R.J. Smith and J.S. Karp, "Post Injection Transmission scanning in a Volume Imaging PET Camera," IEEE Transactions on Nuclear Science, vol. 41, No. 4, Aug. 1994, pp. 1526–1531.

Robert A. deKemp and Claude Nahmias, "Attenuation Correction in PET Using Single Photon Transmission Measurement," Med. Phys., vol. 21, No. 6, Jun. 1994, AM. Assoc. Phys. Med., pp. 771–778.

* cited by examiner

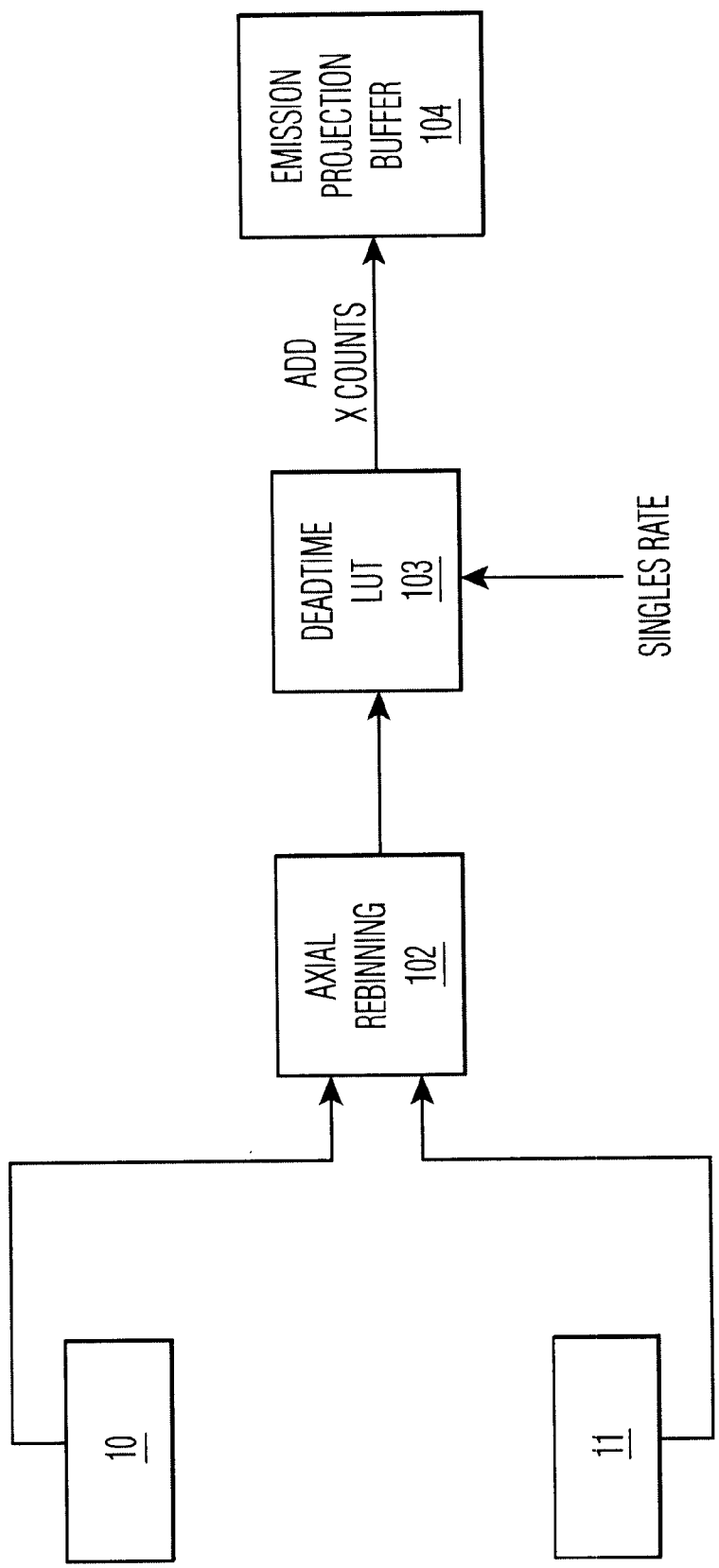

METHOD AND APPARATUS FOR PERFORMING CORRECTION OF EMISSION CONTAMINATION AND DEADTIME LOSS IN A MEDICAL IMAGING SYSTEM

This application is a continuation-in-part of U.S. patent application No. 08/865,930, filed May 30, 1997, which is now U.S. Pat. No. 6,008,493.

FIELD OF THE INVENTION

The present invention pertains to medical imaging systems. More particularly, the present invention relates to correction of emission contamination and deadtime in nuclear medicine imaging systems.

BACKGROUND OF THE INVENTION

In the field of nuclear medicine, images of the internal structures or functions of a patient's body are formed by using gamma cameras to detect radiation emitted from within the body after the patient has been injected with a radiopharmaceutical substance. A computer system generally controls the gamma cameras to acquire data and then processes the acquired data to generate the images. Nuclear medicine imaging techniques include Single-Photon Emission Computed Tomography (SPECT) and Positron Emission Tomography (PET). SPECT imaging is based on the detection of individual gamma rays emitted from the body, while PET imaging is based on the detection of gamma ray pairs that are emitted in coincidence in opposite directions due to electron-positron annihilations. PET imaging is therefore often referred to as "coincidence" imaging.

One factor which has a significant impact on image quality in nuclear medicine is non-uniform attenuation. Non-uniform attenuation refers to the attenuation of radiation emitted from an organ of interest before the radiation can be detected. Such attenuation tends to degrade image quality. A technique which has been used to correct for non-uniform attenuation is transmission scanning, in which gamma radiation is transmitted through the patient to a corresponding scintillation detector and used to form a transmission image. The transmission images provide an indication of the amount of attenuation caused by various structures of the body and can therefore be used to correct for attenuation in the emission images.

For purposes of performing attenuation correction on PET images, transmission scans have commonly been implemented using coincidence transmission sources. However, for various reasons it may be desirable to perform a transmission scan for PET using a single-photon ("singles") source. See, e.g., S. K. Yu et al., "Single Photon Transmission Measurements in Positron Emission Tomography Using $^{137}Cs$," Phys. Med. Biol., vol. 40, 1995, and R. A. deKemp, "Attenuation Correction in Positron Emission Tomography Using Single Photon Transmission Measurement," McMaster University, Hamilton, Ontario, Canada, September 1992. Coincidence events generally represent only a small fraction of the total detected events during an imaging session. Consequently, a singles transmission source is preferable because of its higher associated countrate in comparison to a coincidence transmission source. A higher transmission countrate tends to provide a higher signal-to-noise ratio than a lower countrate does. Because of its higher efficiency and the fact that no coincidence is required, an attenuation correction technique which uses a singles transmission source requires a much shorter acquisition time than an attenuation correction technique which uses a coincidence source. In addition, a technique which uses a singles source tends to suffer less deadtime loss than a technique which uses a coincidence source (i.e., from too much activity at the detector nearest to the source in the coincidence case).

For various reasons, it may be desirable to perform the transmission scan after the patient has been injected with the radiopharmaceutical. For example, post-injection transmission scanning reduces the likelihood of patient motion between the transmission scan and the emission scan, which can degrade image quality. Post-injection transmission scanning also reduces the overall scanning time, because it eliminates the waiting period required for the radiopharmaceutical to reach its best uptake (which is typically close to one hour). One problem with post-injection transmission scanning, however, is that it causes emission radiation to be present during the transmission scan, which may be erroneously detected as transmission radiation. In certain systems, it may be possible to use energy discrimination to distinguish between emission activity and transmission activity, i.e., the transmission radiation and the emission radiation can be distinguished by the differences in their energies. However, energy discrimination becomes less effective if the transmission source and the emission source (the radiopharmaceutical) have photopeaks that are relatively close together in energy. For example, it may be desirable to use a $Cs^{137}$ transmission source with a photopeak at 662 keV in conjunction with a Flouro Deoxi Glucose (FDG) coincidence emission source with a photopeak at 511 keV. Because, the photopeaks are so close together, some of the emission photons may have energy values that fall within the transmission energy acceptance window. As a result, some of the emission photons may be incorrectly detected as transmission photons, introducing artifacts into the transmission image. This effect is referred to as emission contamination of a transmission scan.

Therefore, it is desirable to have a technique for correcting for emission contamination of a transmission scan in a nuclear camera system. It is further desirable that such a technique take into consideration and correct for spatial variations in the emission activity. In addition, it is desirable that such a technique can be used to correct for emission contamination of a transmission scan which uses a singles transmission source.

Another common problem in nuclear medicine is deadtime loss. Deadtime refers to the inability of a gamma camera detector to distinguish between two radiation-induced scintillation events which occur very close together in time due to the time required to process individual events. Deadtime loss can be defined as the difference between the true countrate ("singles rate") and the observed countrate which results from detector deadtime. In an ideal system in which there is no deadtime loss, the observed countrate equals the true countrate. In contrast, in a system that is subject to deadtime loss, the observed countrate is lower than the true countrate.

One technique for correcting for deadtime loss is to apply a single, global correction factor, which is applied after the data has been acquired. See, e.g., R. J. Smith et al., "Simultaneous Post Injection Transmission and Emission Contamination Scans in a Volume Imaging PET scanner," 1995 IEEE Nuclear Science Symposium and Medical Imaging Conference Record, vol. 3, pages 1781–85, 1995. The use of a global correction factor, however, has disadvantages. In particular, deadtime loss is dependent upon the singles rate; as the singles rate increases, the deadtime loss also increases. Because the singles rate varies spatially (i.e., depending on projection angle and, if an axially moving transmission source is used, axial position), the deadtime loss is spatially dependent. Therefore, the use of a global deadtime correction factor does not account for the spatial dependency of deadtime losses and may therefore result in inaccuracies in the transmission image. Hence, it would be desirable to have a technique for deadtime correction which takes into consideration the spatial dependencies of deadtime losses. It would be further desirable to have such a technique which also corrects for emission contamination in a transmission scan with the advantageous features discussed above.

SUMMARY OF THE INVENTION

The present invention includes a method and apparatus for correcting data corresponding to detected radiation in a medical imaging system. Radiation-induced events are detected, and data of an object to be imaged are generated based on the detected events. The data are corrected for emission contamination, deadtime, or both. For either type of correction, the correction may be performed in real-time or as post-processing. In either case, the correction further may be performed on an event-by-event basis or on grouped data. Images of the object are then generated based on the corrected data.

Other features of the present invention will be apparent from the accompanying drawings and from the detailed description which follows.

BRIEF DESCRIPTION OF THE DRAWINGS

The present invention is illustrated by way of example and not limitation in the figures of the accompanying drawings, in which like references indicate similar elements and in which:

FIG. 14D is a block diagram illustrating a technique for performing real-time correction of emission data for deadtime.

DETAILED DESCRIPTION

Figure 1:
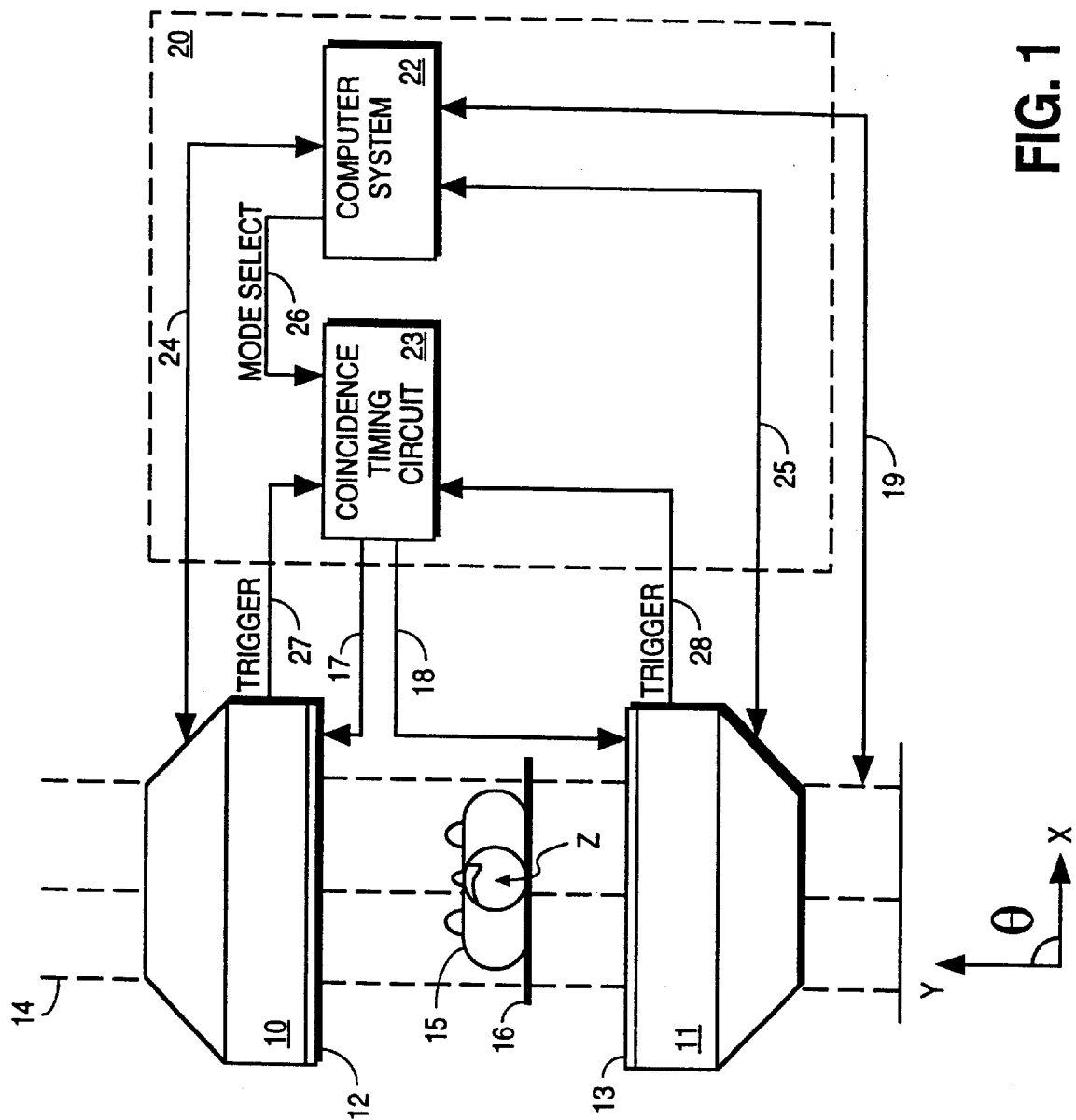
FIG. 1 is a block diagram of a dual PET/SPECT gamma camera system.

A method and apparatus for correcting for emission contamination and deadtime loss in a nuclear medicine imaging system are described. Certain aspects of the present invention relate to attenuation correction of PET images in a dual-detector gamma camera system capable of both SPECT and PET imaging. An example of such a system is illustrated in FIG. 1 in block diagram form. A gamma camera system having dual SPECT/PET capability is described in detail in U.S. Pat. No. 5,585,637 and U.S. Pat. No. 5,608,221, both issued to Bertelsen et al. Certain aspects of such capability are described below as background information. In addition, although the following description relates to an embodiment of the present invention having two gamma camera detectors, the present invention is not limited to a two-detector system.

The dual-mode gamma camera system 1 of FIG. 1 includes a processing system 20 coupled to a pair of scintillation detectors 10 and 11. The detectors 10 and 11 have imaging surfaces 12 and 13, respectively. The detectors 10 and 11 are mounted on a gantry 14, which can rotate the detectors 10 and 11 either individually or in unison about an axis of rotation, z (the "z axis"), which is perpendicular to the x-y plane. A patient 15 to be imaged rests on a table 16 between the detectors 10 and 11. The detectors are shown configured in a 180 degree orientation (i.e., offset 180 degrees relative to each other about the axis of rotation), as may be appropriate for coincidence (PET) imaging. Generally, the processing system 20 controls the gantry 14 to provide movement of the detectors 10 and 11, controls the mode (PET vs. SPECT) of the detectors 10 and 11, receives data acquired by the detectors 10 and 11, and generates images from that data. Each of the detectors 10 and 11 includes a scintillation crystal, an array of photomultiplier tubes (PMTs) arranged in a conventional two dimensional matrix, and various processing circuitry. Gamma camera detectors such as detectors 10 and 11 are well-known in the art; accordingly a detailed description of the internal components of detectors 10 and 11 and their operation is not =necessary to an understanding of the present invention and is not provided herein. The scintillation crystals can be composed of sodium iodine (NaI) and may be located between a collimator (not shown) and the PMT array.

The processing system 20 includes a programmable coincidence timing circuit (CTC) 23 coupled to the detectors 10 and 11 and coupled to a computer system 22. Note that in other embodiments, a CTC 23 may be included in one or both of the detectors 10 and 11. The computer system 22 may be, or may include, for example, a conventional personal computer (PC), workstation, single-board computer, or a combination of such devices. Note that in alternative embodiments, however, some of the described functions of the computer system 22, or aspects thereof, may instead be implemented within one or more of the detectors 10, the gantry, or in other distinct modules. Thus, computer system 22 may be embodied as two or more physically distinct processing systems.

A signal 26 from the computer system 22 indicates to the CTC 23 the current mode of operation (i.e., SPECT or PET). Upon detection of a scintillation event in either detector 10 or 11, lines 27 and 28, respectively, carry trigger pulses to CTC 23. CTC unit 23 then generates valid event trigger signals over lines 17 and 18 for the detectors 10 and 11, respectively, according to the selected mode of operation (SPECT or PET). The valid event trigger signals 17 and 18 are used by the detectors 10 and 11 to start (or reset) their accumulators (integrators), which accumulate (integrate) the energy of detected scintillation events and are therefore called "valid event" trigger signals. In the PET mode, integration is not started until a coincidence is detected between detector 10 and 11. In SPECT mode, an integration is started for each detector upon a trigger event, regardless of coincidence. After integration and centroiding, the detectors 10 and 11 output over lines 24 and 25, respectively, X and Y position values and Z energy values.

Figure 2:
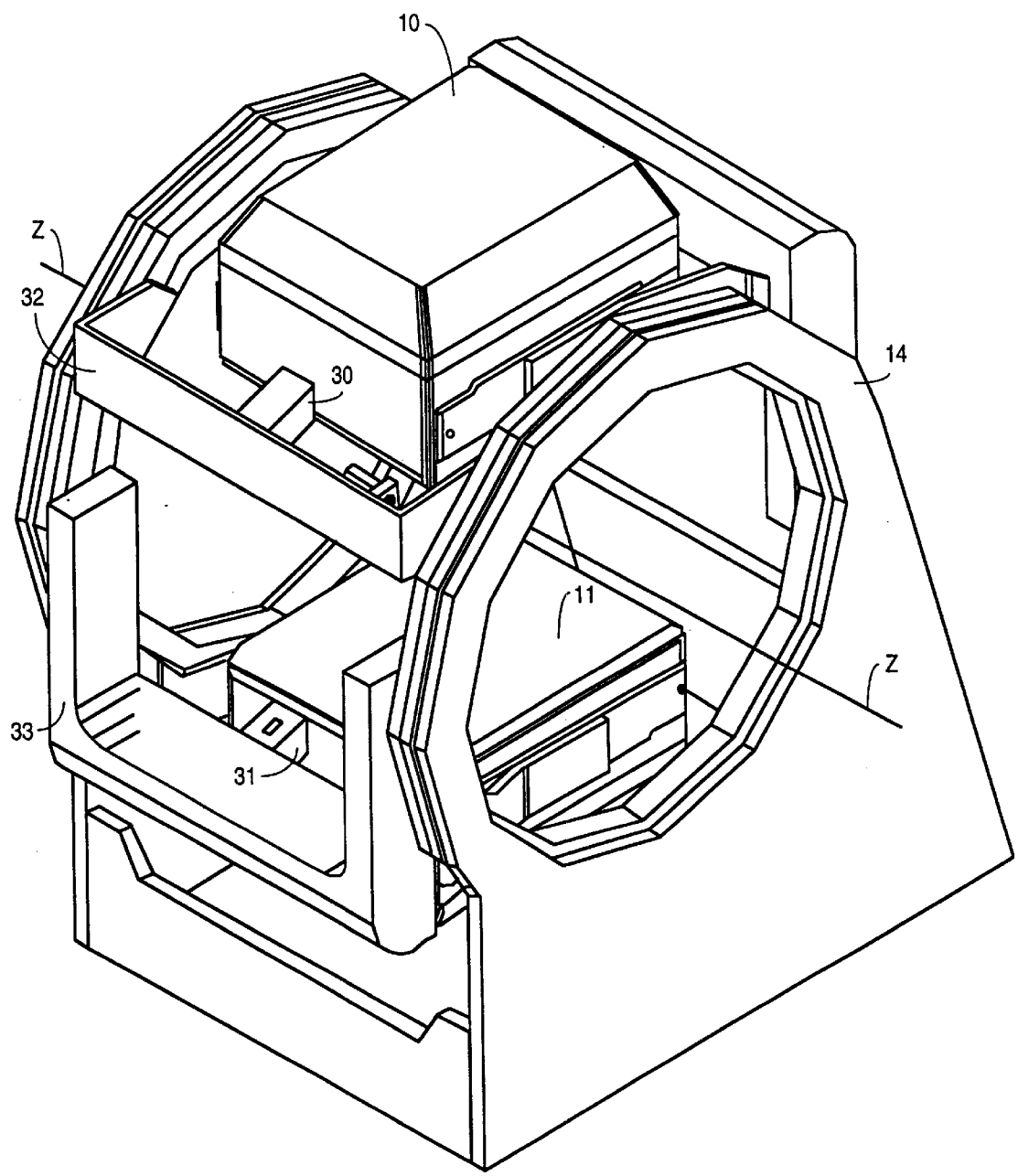
FIG. 2 is a perspective view of the gantry and detectors of the gamma camera system of FIG. 1.

FIG. 2 illustrates a perspective view of the gantry 14 and detectors 10 and 11, according to one embodiment. FIG. 2 also shows two transmission source assemblies 30 and 31 for performing transmission scans. As will be described below, each of the transmission source assemblies 30 and 31 includes a single-photon ("singles") mode radiation source used to perform transmission scans for correcting PET images for the effects of attenuation. In one embodiment, each of the source assemblies 30 and 31 includes a $Cs^{137}$ point source. As will be described below, each of the source assemblies 30 and 31 includes appropriate shielding as well as collimation designed to provide a specific illumination profile. Source assembly 30 is mounted to a track assembly 32 adjacent to detector 10 and outside the field of view (FOV) of detector 10. Source assembly 30 has an aperture and is mounted so that the aperture faces detector 11 to allow radiation from source assembly 30 to illuminate detector 11. Similarly, source assembly 31 is mounted to a track assembly 33 adjacent to detector 11 and outside the FOV of detector 11. Source assembly 31 further has an aperture and is mounted so that the aperture faces detector 10 to allow radiation from source assembly 31 to illuminate detector 10. Track assemblies 32 and 33 provide a mechanism for translating the source assemblies along the z axis in one embodiment of the present invention. Track assemblies 32 and 33 are rotatable about the z axis in unison with detectors 10 and 11; consequently, the point sources 30 and 31 at all times remain fixed relative to detectors 10 and 11 in terms of their angular positions about the z axis.

Figure 3:
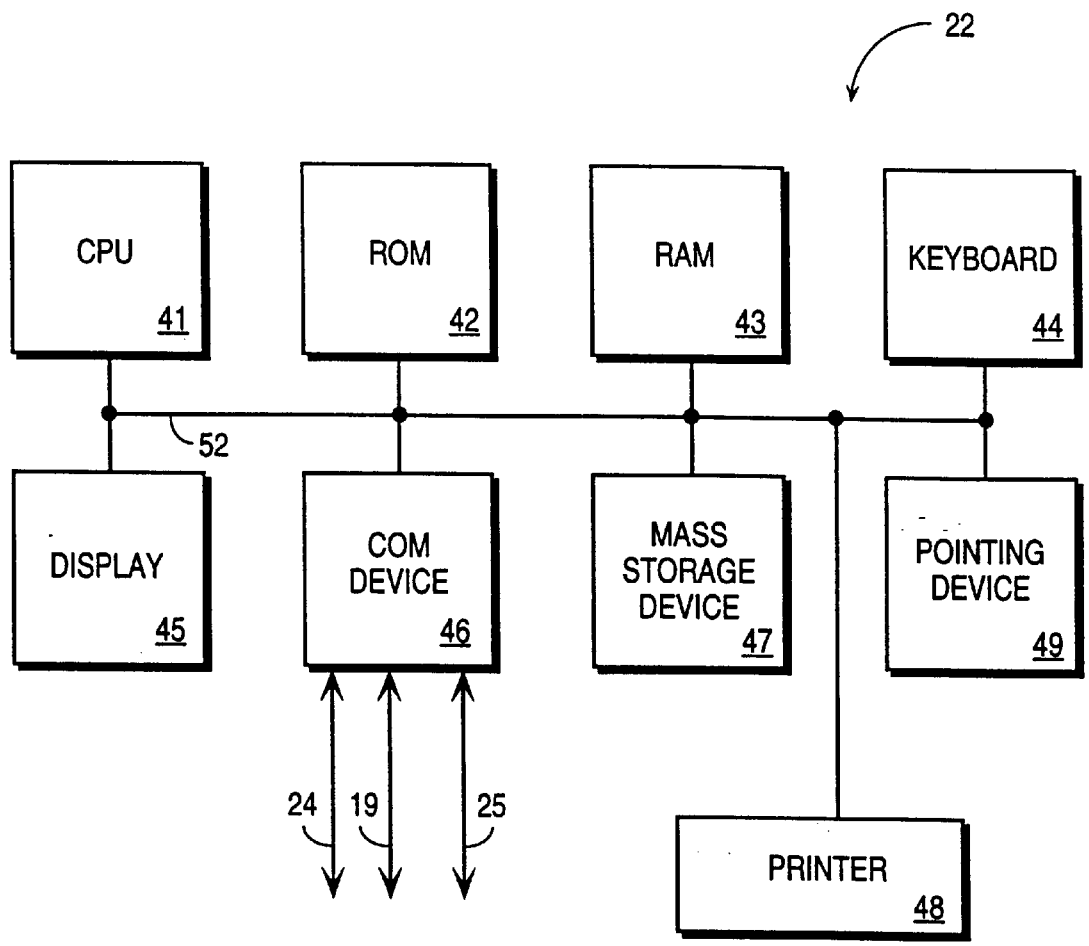
FIG. 3 is a block diagram of the computer system of the gamma camera system of FIG. 1.

FIG. 3 illustrates a block diagram of the computer system 22. In the illustrated embodiment, the computer system 22 comprises a central processing unit (CPU) 41, a read-only memory (ROM) 42, and a random access memory (RAM) 43, each coupled to a bus 52 for communicating information within the system 22. Note that the bus 52 may comprise multiple physical buses coupled together by various bridges, controllers, and/or adapters. Also coupled to the bus 52 are a mass storage device 47, such as a magnetic or optical disk and disk drive; a display device 45, such as a cathode ray tube (CRT) or liquid crystal display (LCD); an alphanumeric keyboard 44; a pointing device 49, such as a mouse, trackball, or touchpad; and, a communication device 46. The communication device 46 includes a high speed communication port for communicating with the gantry 14 and detectors 10 and 11 via signals 19, 24 and 25.

The computer system 22 executes software instructions to implement procedures according to the present invention and various other functions. Specifically, the CPU 41 may be configured to perform certain steps in accordance with the present invention by software instructions stored in RAM 43, ROM 42, mass storage device 47, or a combination of these devices.

Figure 4:
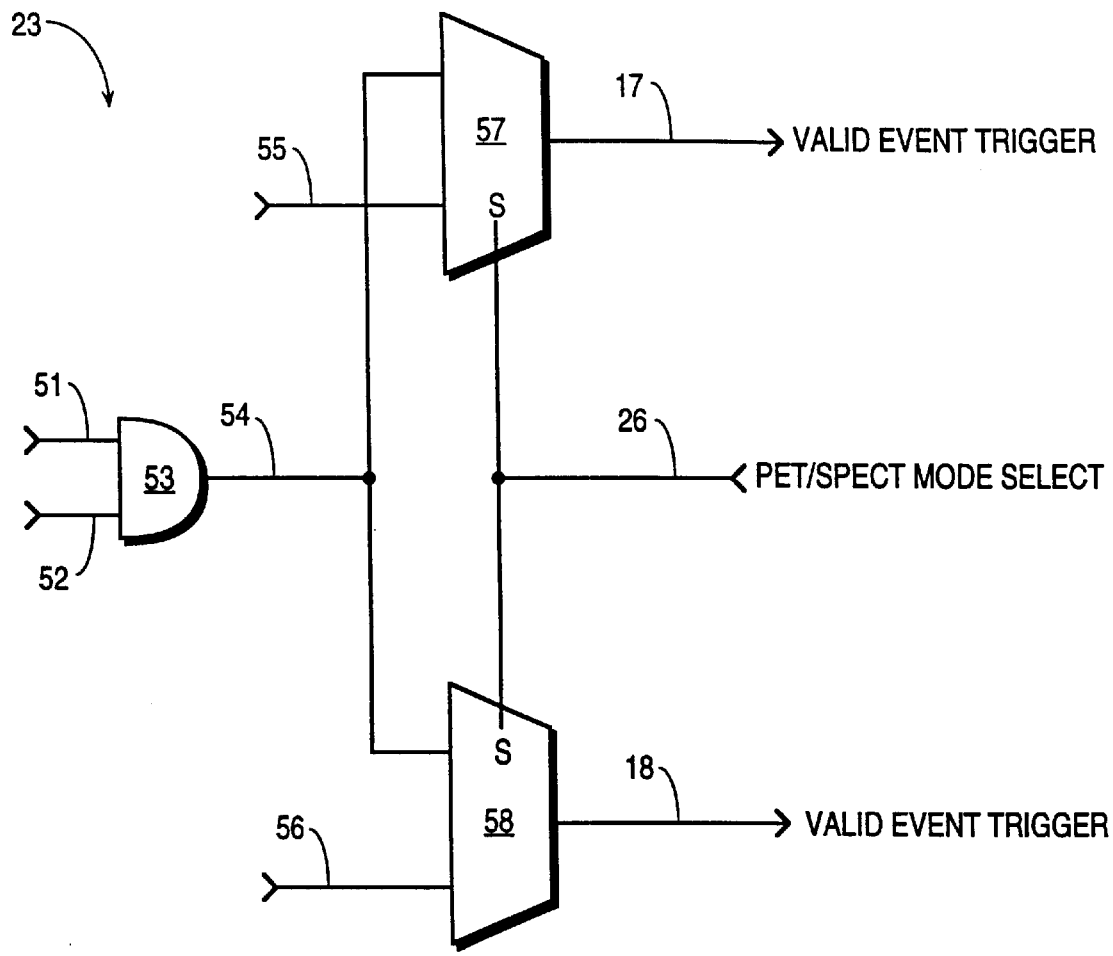
FIG. 4 illustrates a coincidence timing circuit for switching between PET and SPECT modes.

As noted above, the CTC 23 (see FIG. 1) is used to control the operational mode (SPECT or PET) of the gamma camera system 1. FIG. 4 illustrates one embodiment of the CTC 23 in greater detail. FIG. 4 shows four signals, 51, 52, 55, and 56. Signals 51 and 55 are trigger signals generated by detector 10 in response to scintillation events and are provided to CTC 23 over line 27. Signal 55 is generated by SPECT detection electronics in detector 10, and signal 51 is generated by PET detection electronics in detector 10. Signals 52 and 56 are trigger signals generated by detector 11 in response to scintillation events and are provided to CTC 23 over line 28. Signal 56 is generated by SPECT detection electronics in detector 11 while signal 52 is generated by PET detection electronics in detectors 11. Signals 51 and 52 from the PET detection electronics of detectors 10 and 11, respectively, are provided as inputs to an AND gate 53. AND gate 53 outputs a signal 54, which is asserted only if signals 51 and 52 are in coincidence (i.e., both asserted within a predetermined time window). The CTC 23 also includes two double-input multiplexors 57 and 58. Multiplexor 57 receives as input signal 55 from the SPECT detection electronics of detector 10 and signal 54 from AND gate 53. Multiplexor 58 receives as input signal 56 from the SPECT detection electronics of detector 11 and signal 54 from AND gate 53.

A mode selection control signal 26 is coupled to the select inputs of multiplexors 57 and 58. The control signal 26 is used to switch between PET and SPECT modes of operation. The control signal 26 may result from a command entered by a user through a user interface provided by the computer system 22. When the control signal 26 has a value indicating PET mode is desired, then an asserted signal over line 54 passes over both line 17 to detector 10 and over line 18 to detector 11 as valid event trigger signals. When the control signal 26 has a value indicating SPECT mode is desired, then the signal over line 55 is carried over line 17 to detector 10, and the signal over line 56 is carried over line 18 to detector 11 as valid event trigger signals. Signals over line 17 are used to trigger event integrators in the detection circuitry of detector 10, and signals over line 18 are used to trigger event integrators in the detection circuitry of detector 11.

Singles-Mode Fanbeam Transmission Scan

Figure 5A:
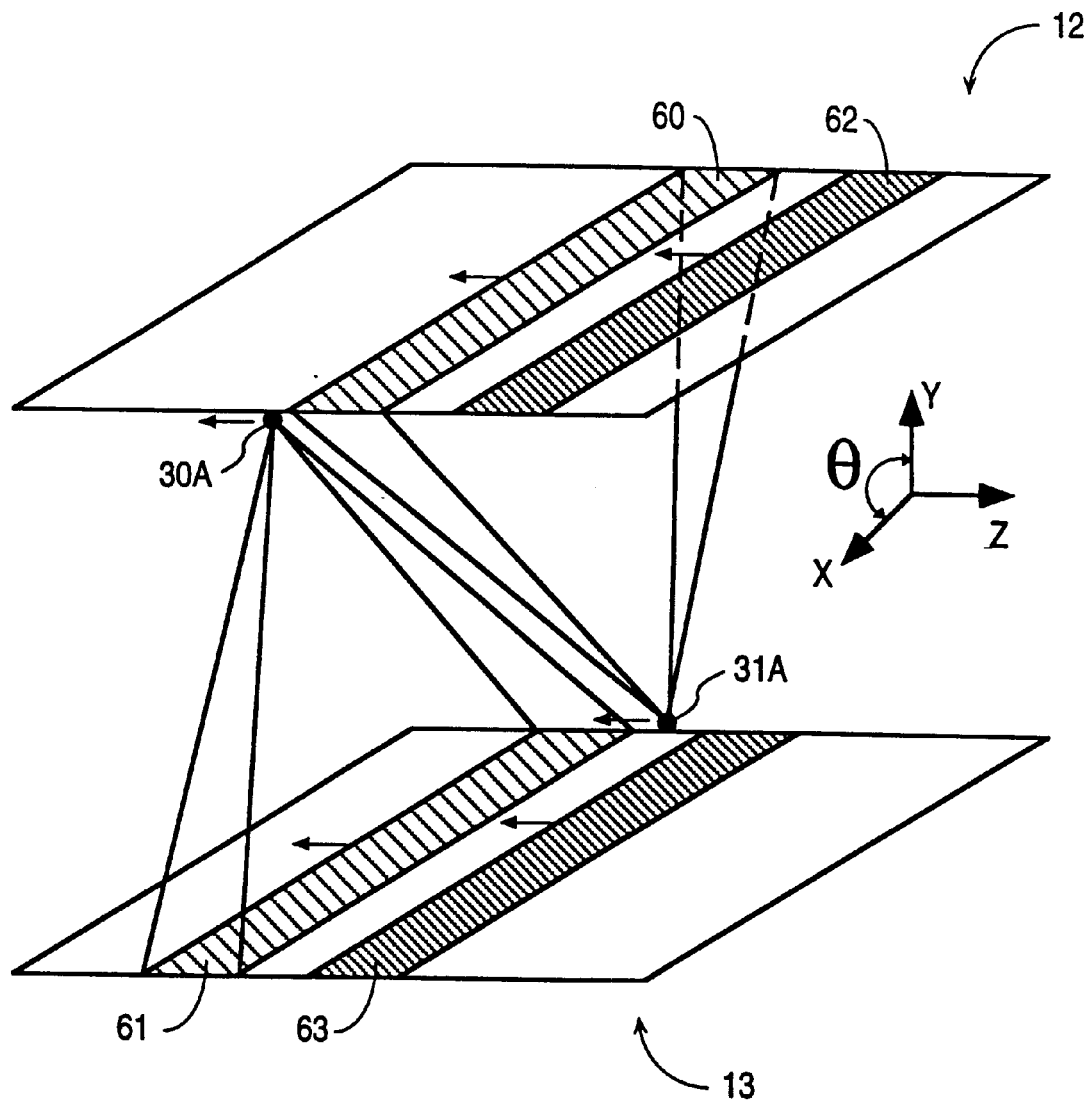
FIG. 5A illustrates two radiation point sources illuminating two corresponding detector imaging surfaces using fanbeam illumination profiles.
Figure 5B:
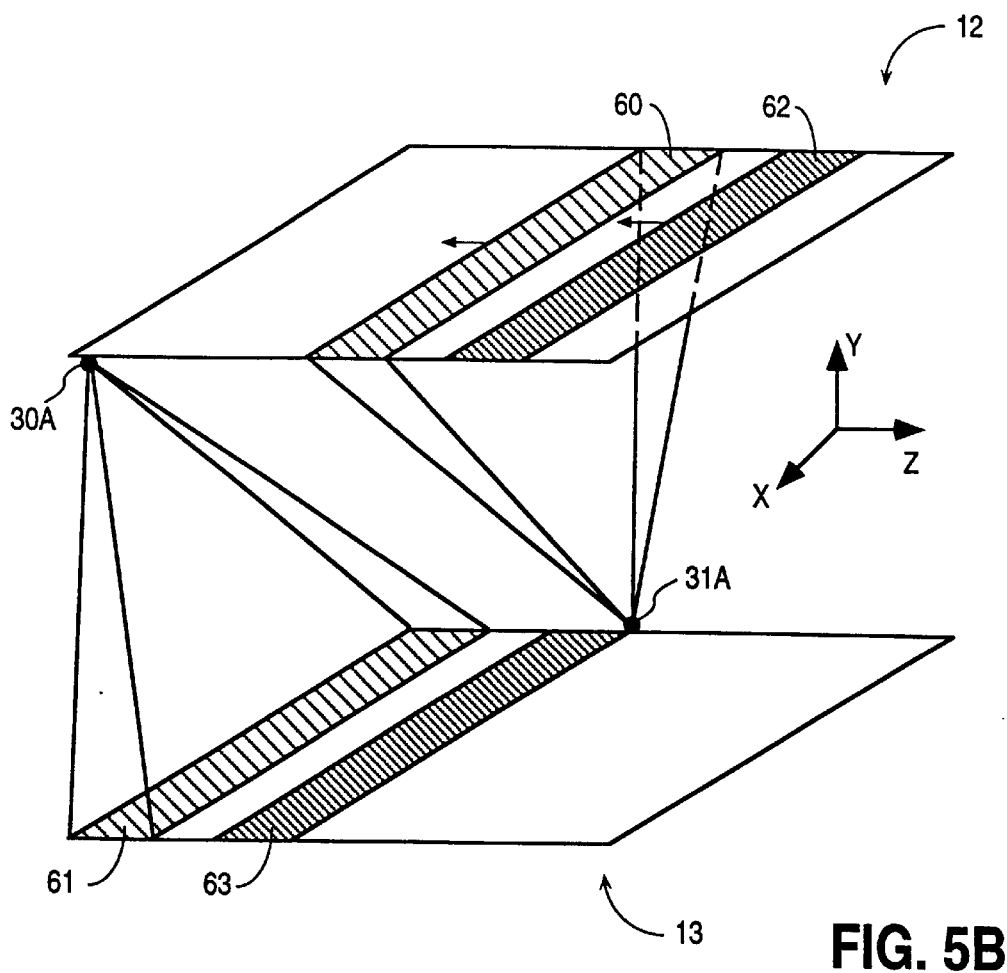
FIG. 5B illustrates two axially offset radiation point sources illuminating two corresponding detector imaging surfaces using fanbeam illumination profiles.

The present invention includes the use of two singles-mode radiation point sources to perform a transmission scan for purposes of performing attenuation correction on coincidence (PET) data. In one embodiment, each of the point sources is a $Cs^{137}$ source having an energy peak at 662 keV. In the embodiment of FIG. 2, source assemblies 30 and 31 are mounted on the same side of the detectors 10 and 11 in the transaxial (x) direction. FIGS. 5A and 5B illustrate an alternative embodiment in which the source assemblies 30 and 31 are mounted on opposite sides of detectors 10 and 11 in the transaxial direction. Referring now to FIG. 5A, source assemblies 30 and 31 (not shown) contain $Cs^{137}$ point sources 30A and 31A, respectively. Point source 30A is mounted adjacent to the imaging surface 12 of detector 10, while point source 31A is mounted adjacent to the imaging surface 13 of detector 11. As indicated above, the point sources 30A and 31A remain fixed relative to detectors 10 and 11 in terms of their angular positions about the z axis.

Transmission detection (spatial) windows 60 and 61 are defined on the imaging surfaces 12 and 13 of detectors 10 and 11, respectively, for detecting transmission radiation transmitted from sources 31A and 30A, respectively. The transmission detection windows 60 and 61 are defined electronically by the detectors and/or the computer system 22 in a manner that is well-known in the art. The transmission detection windows 60 and 61 are defined for detection of photons within an energy range centered at 662 keV. Transmission detection window 60 is aligned with source 31A relative to the z axis ("axially"), and transmission detection windows 61 is defined so that it is aligned axially with source 30A. In the embodiment of FIG. 5A, the point sources 30A and 31A are offset axially by an amount that is small relative to the axial field of view (FOV) of detectors 10 and 11, such that transmission detection windows 60 and 61 are substantially adjacent in the z direction. This offset reduces transmission self-contamination (i.e., the undesirable detection of transmission radiation by the detector nearest to the transmitting source), which is discussed further below.

Also defined on the imaging surfaces 12 and 13 are emission contamination detection windows 62 and 63, respectively. The emission contamination detection windows 62 and 63 are used for purposes of correcting for emission contamination of the transmission scan, as will be described below.

During transmission scanning, the point sources 30A and 31A are scanned synchronously across the FOVs of detectors 10 and 11 along the z axis. Further, transmission detection windows 60 and 61 are scanned synchronously with their corresponding point sources, 31A and 30A. Only radiation detected within transmission detection windows 60 and 61 is recognized for purposes of acquiring a transmission data set (i.e., projection). In addition, each of the source assemblies 30 and 31 (see in FIG. 2) includes collimation designed to produce a fanbeam illumination profile, as shown in FIG. 5A, to substantially limit transmission radiation to transmission detection windows 60 and 61, respectively.

It may be desirable to have a greater axial offset between the point sources 30A and 31A than that shown in FIG. 5A. Accordingly, FIG. 5B illustrates an alternative embodiment having a greater offset. A larger axial offset between the point sources 30A and 31A may further reduce transmission self-contamination as well as cross-scatter of transmission radiation into the wrong detection window.

During a PET imaging session, the detectors 10 and 11 are arranged in a 180° orientation, and are used to detect emission radiation from a number of angular positions about the z axis. Accordingly, at each of these angular positions about the z axis, a transmission scan is performed by scanning the transmission radiation fanbeams and the corresponding transmission detection windows 60 and 61 axially across the FOVs of the detectors 10 and 11. Scanning of the fanbeams may be accomplished by translating the source assemblies 30 and 31 axially.

In an alternative embodiment, scanning can be performed by maintaining the point sources in a fixed position along the z axis and using a rotating aperture to scan the fanbeam across the FOV of the opposing detector. In such an embodiment, the count density at the corresponding detector will vary depending upon the inclination angle of the fanbeam. For example, the count density will tend to decrease as the distance between the source and the illuminated portion of the detector increases and, consequently, the illuminated area on the detector increases. However, assuming the camera system is calibrated using a blank transmission scan (i.e., no object in the field of view), as is conventional practice in nuclear imaging, these effects will be normalized out when the actual images are generated.

In yet another embodiment, the transmission scan may be performed by maintaining fixed axial (z) positions of the sources 30A and 31A while each of the sources 30A and 31A illuminates the entire imaging surface of the corresponding detector, rather than scanning a radiation beam across the imaging surface. In this embodiment, a single-slice rebinning algorithm may be adequate if the effective axial field of view is sufficiently small, such that the incident angle at which the transmission radiation impinges upon the detector surface is close to 90 degrees. However, if the axial field of view to be scanned is relatively large, such that the incident angle becomes more acute, it may be desirable to use a three-dimensional rebinning algorithm An example of a three-dimensional rebinning algorithm which may be used is the Fourier rebinning technique, which is described by M. Defrise et al., "Exact and Approximate Rebinning Algorithms for 3-D PET Data," IEEE Transactions on Medical Imaging, vol. 16, No. 2, April 1997.

Figure 6:
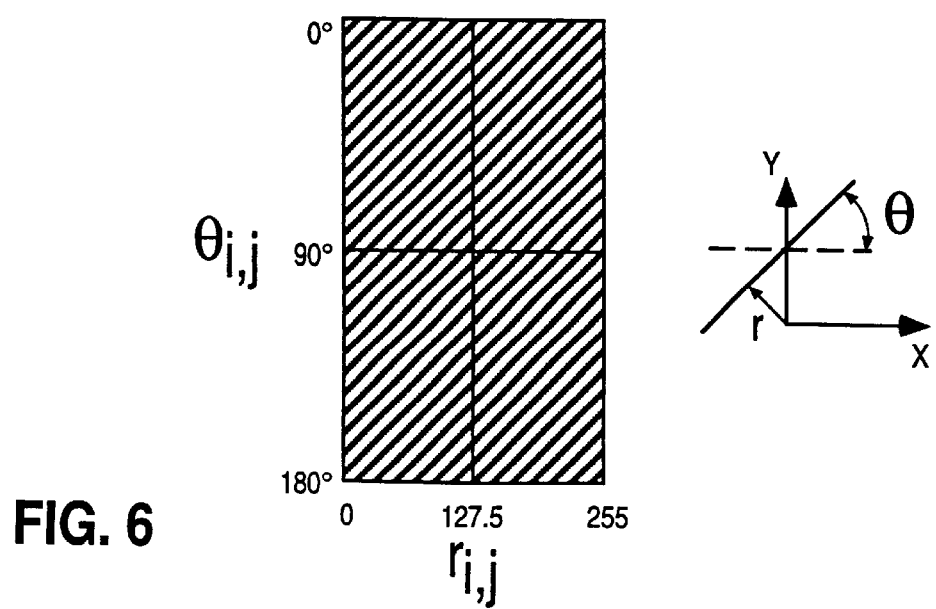
FIG. 6 illustrates an example of a sinogram which may be obtained using the configuration of FIGS. 5A with only one detector operating.

The geometry illustrated in FIGS. 5A results in a base pattern sinogram similar to that illustrated in FIG. 6 (for one detector) for 32 angular stops over 360° of rotation of the detectors and point sources. In FIG. 6, the diagonal lines regions represent regions of sinogram space in which data is acquired, while the gaps between the lines represent regions in which there is no coverage. This effect occurs when the sinogram is generated by taking all of the possible 1024 different transverse positions that a detector can produce and then calculating the corresponding r and θ. Such gaps in the sinogram may produce artifacts in the reconstructed images. Therefore, it may be desirable for the rebinning software to circumvent this effect. A solution is to store raw detector coordinates and, during post-processing, fill in the sinogram by searching for and interpolating amongst the possible raw image (projection) locations that could have contributed to a particular point in the sinogram.

Figure 7:
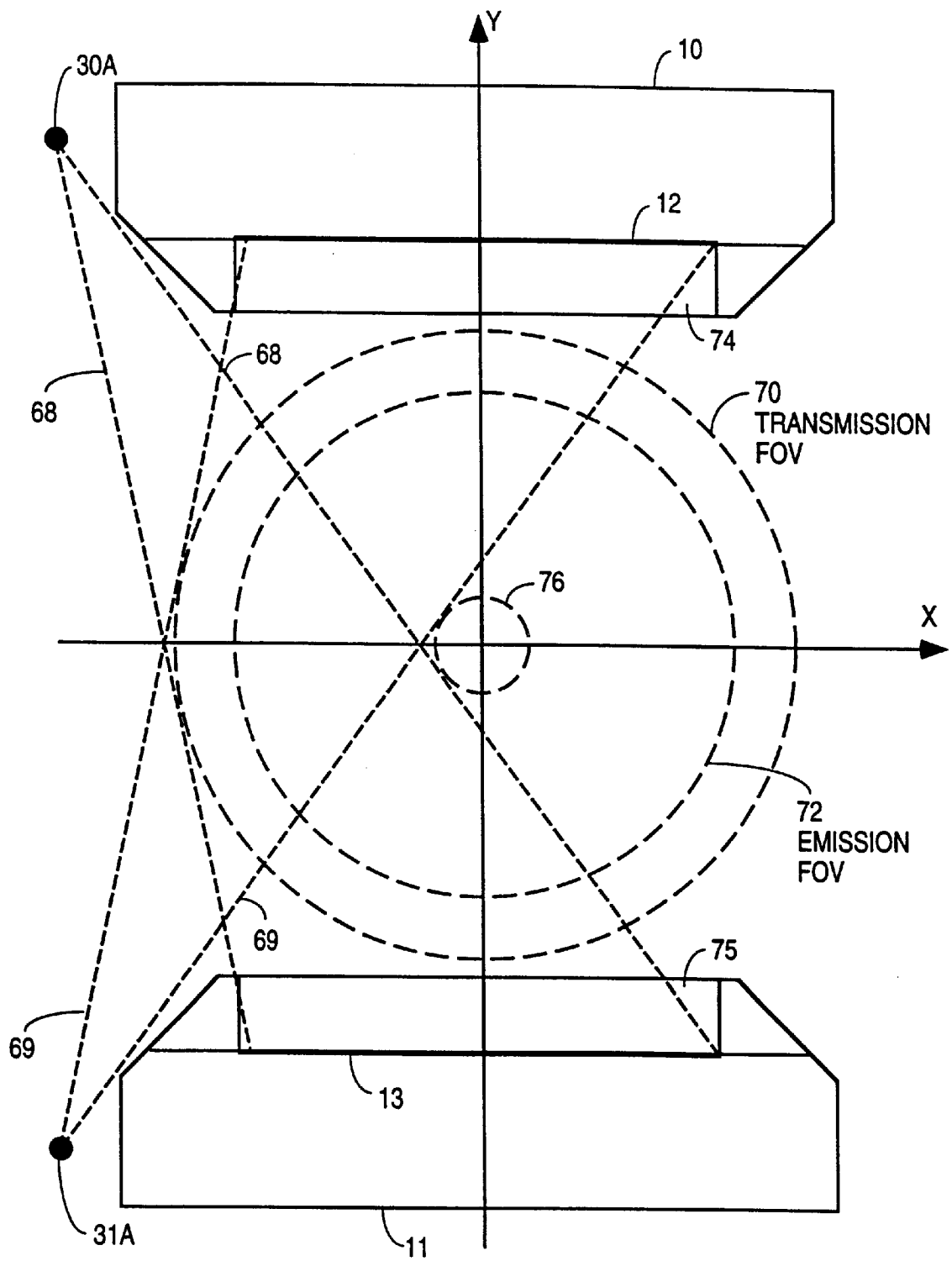
FIG. 7 illustrates an axial view of radiation point sources and detectors in relation to the fields of view of the detectors.

FIG. 7 illustrates the geometry associated with the transmission scanning of the present invention in terms of the FOVs of the detectors 10 and 11 for one embodiment. Specifically, FIG. 7 illustrates a view in a transverse (x-y) plane according to an embodiment in which the sources 30A and 31A are on the same side of detectors 10 and 11 in the transaxial (x) direction. In FIG. 7, septa 74 and 75 are disposed along the imaging surfaces 12 and 13 of detectors 10 and 11, respectively. Point sources 30A and 31A are mounted outside the FOVs of detectors 10 and 11. Such mounting avoids blocking the detectors and reduces transmission self-contamination. As noted above, a transmission scan across the entire axial width of detectors 10 and 11 is performed at each angular stop about the z axis. The aggregate effect of these transmission scans with the illustrated placement of point sources is a transmission FOV (in each transverse slice) represented by circle 70. The emission field of view (in each transverse slice) is represented by circle 72.

In one embodiment, the point sources 30A and 31A are mounted outside the FOVs of detectors 10 and 11, such that the detectors themselves limit the allowable beamwidth (in the transverse plane) of the fanbeams generated by sources 30A and 31A. In such an embodiment, the transmission FOV 70 is defined by two boundaries, an outside boundary and an inside boundary. The outside boundary is defined by the outer edges of the transmission fanbeams 68 and 69 at each of the angular stops about the z axis, while the inside boundary is defined by the circumference of circle 76. Thus, circle 76 represents a gap, or blind spot, in the transmission field of view 70. In order to prevent this gap from resulting in incomplete data acquisition, the computer system 22 causes the table 16 (FIG. 1) to move vertically and horizontally relative to the z axis in dependence on the angular positions of the detectors 10 and 11 about the z axis in order to provide full coverage of the object of interest. Such table motion effectively increases the transmission FOV 70. In one embodiment, table motion is controlled by the gantry 14, which includes a dedicated microprocessor (not shown). A technique for providing table motion in a medical imaging system is described in U.S. Pat. No. 5,444,252 of Hug et al., which is assigned to the assignee of the present invention.

Figure 8A:
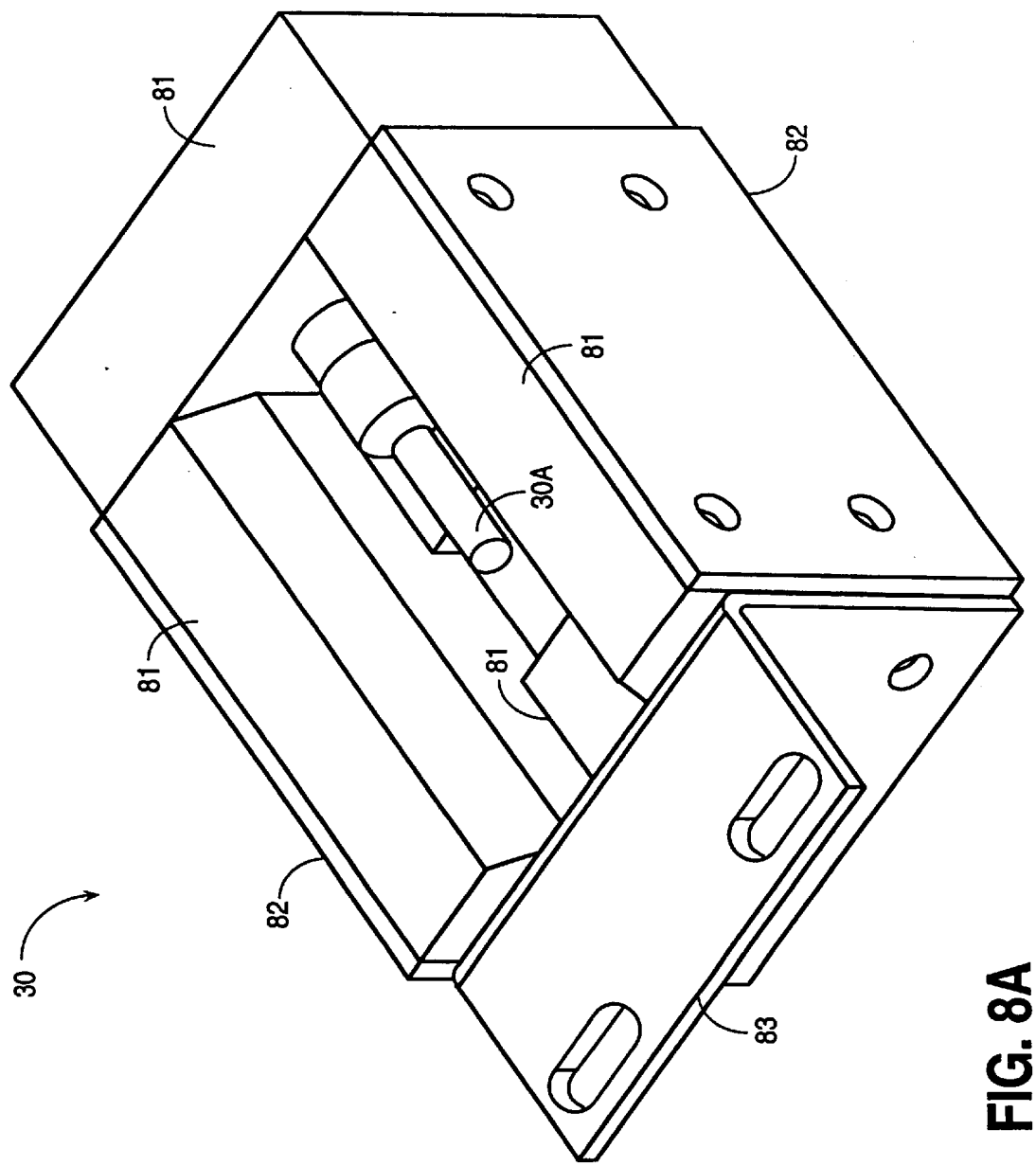
FIG. 8A illustrates a radiation point source assembly.

FIG. 8A illustrates the point source assembly 30 according to one embodiment. It should be noted that point source assembly 31 is substantially identical to point source assembly 30 unless specifically stated otherwise. The assembly 30 includes a number of lead shielding structures 81, which partially enclose the point source 30A. The lead structures 81 are encased by aluminum or steel brackets 82 and 83. Bracket 83 forms a means for mounting source assembly 30 to track assembly 32 (see FIG. 2) to allow axial translation of source assembly 30.

Figure 8B:
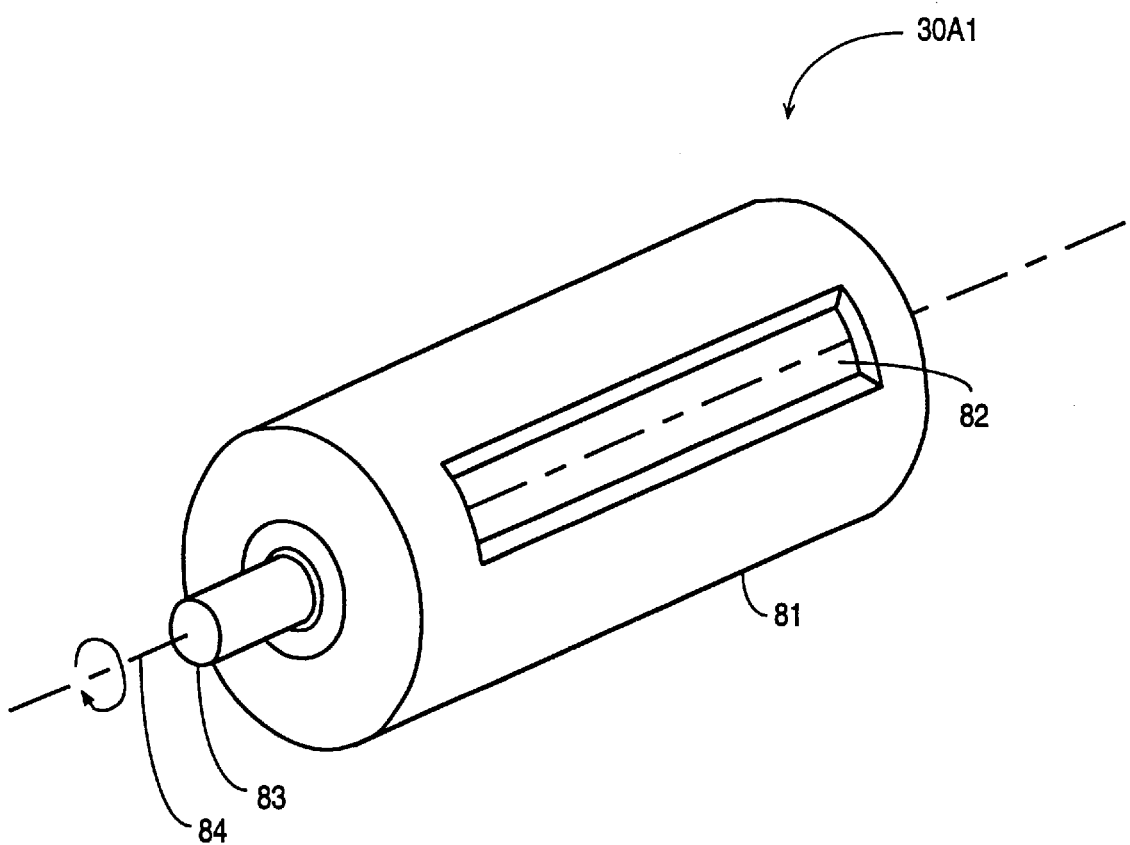
FIG. 8B illustrates a radiation point source assembly according to an embodiment using a rotating aperture.

FIG. 8B shows an alternative embodiment of a point source assembly or use in an embodiment in which the point sources are not translated along the z axis in order to provide the scanning of the fanbeam. The source assembly 30A1 is fixed axially but includes an aperture 82 that is rotated about an axis 84 to provide the scanning of the fanbeam. The source assembly 30A1 is mounted appropriately to the gantry 14 with axis 84 is parallel to the x axis. The point source in this embodiment (not shown) is encased with appropriate shielding 81 similar to that of assembly 30A in FIG. 8A. The casing 81 and aperture 82 are rotated about a shaft 83 (i.e., about axis 84).

Figure 9A:
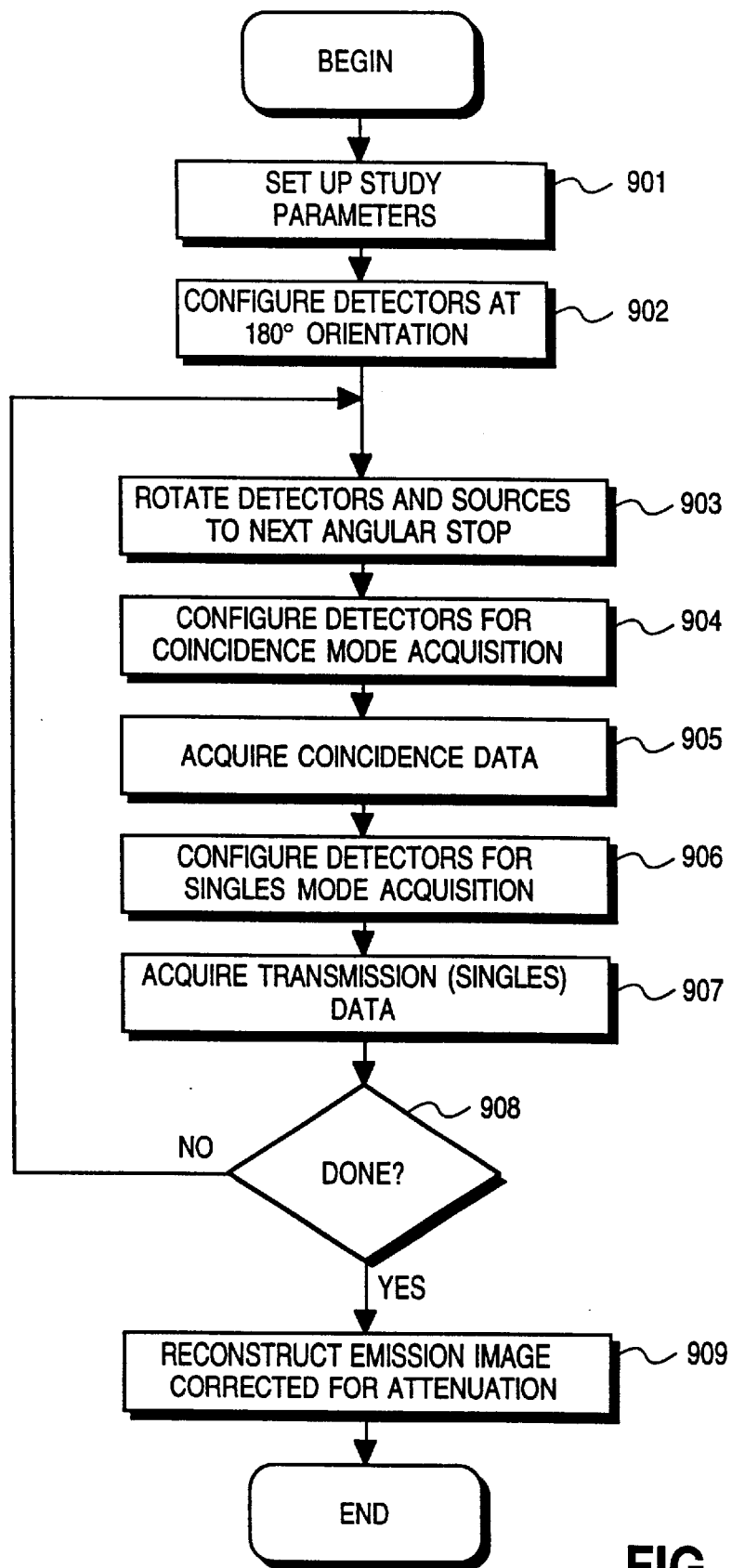
FIGS. 9A and 9B are flow diagrams illustrating overall routines for generating attenuation corrected PET images according to two different embodiments.

FIG. 9A illustrates an overall routine according to one embodiment for acquiring both coincidence (emission) data for a PET study, as well as singles transmission data for attenuation correction of the coincidence data. In step 901, the initial study parameters are set up in the computer system 22. These parameters include, for example, the total number of angular stops about the z axis and the total acquisition time at each stop for both the emission scan and transmission scan. Next, in step 902, the detectors 10 and 11 are configured in a 180° orientation about the z axis to enable coincidence detection. In step 903 the detectors 10 and 11 are rotated (together with source assemblies 30 and 31) to the first (or next) angular stop about the z axis. In step 904, the detectors are configured for detection of emission data in coincidence mode. After acquiring coincidence data for the prescribed time period in step 905, the detectors are then configured for detection in the singles mode in step 906. Next, in step 907, a transmission scan is performed in the manner described above (i.e., by scanning the transmission radiation fanbeams across the detector imaging surfaces), and the transmission data is acquired as singles data. If there are additional angular stops at which data is to be acquired (step 908), then the routine repeats from step 903. Otherwise, in step 909 the emission image is reconstructed and corrected for attenuation using the transmission image data.

Figure 9B:
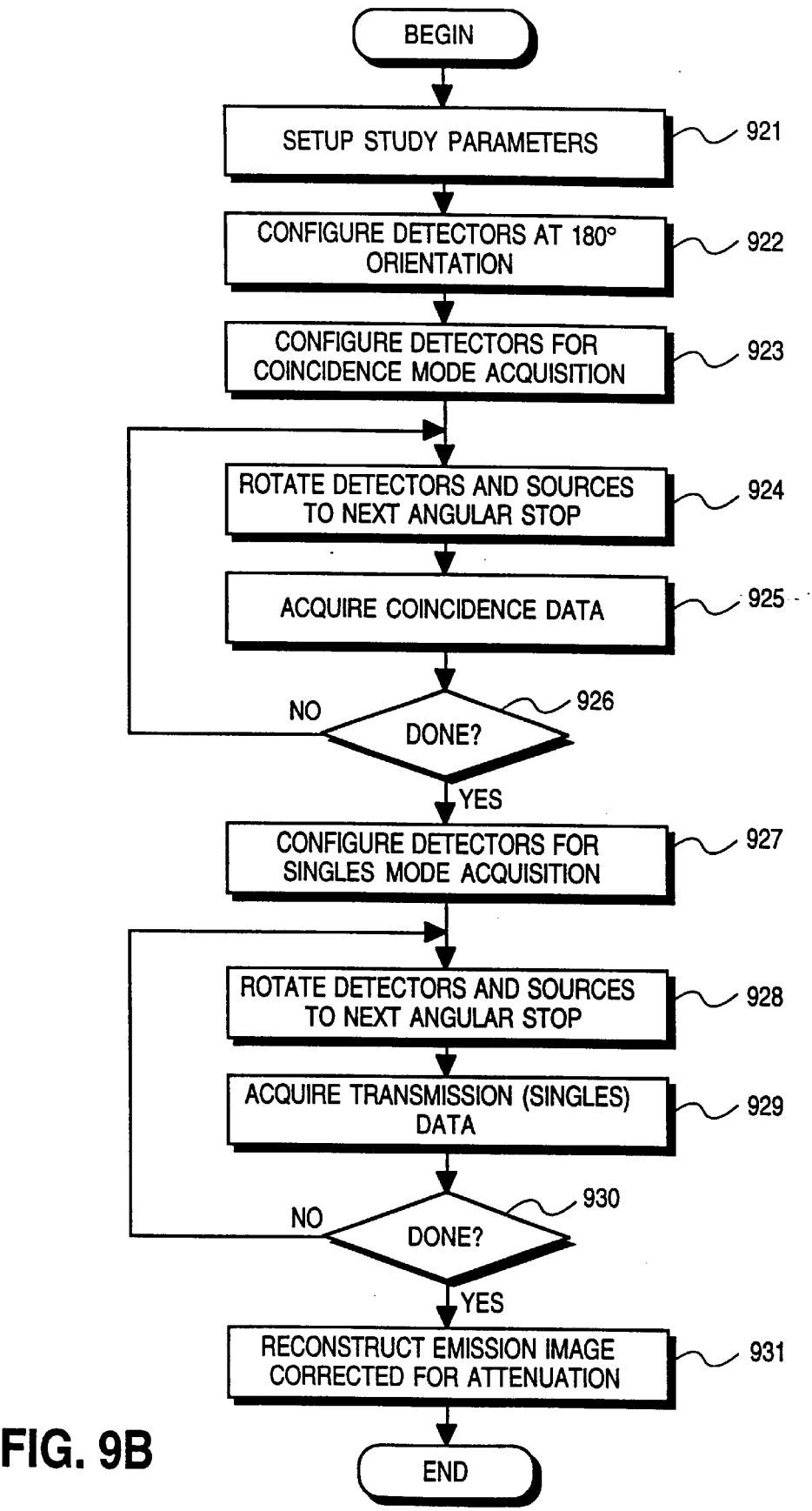

FIG. 9B illustrates another overall routine for acquiring both coincidence (emission) data for a PET study and transmission data for attenuation correction, according to a second embodiment. In the embodiment of FIG. 9B, the emission data is acquired first followed by acquisition of transmission data. More specifically, the study parameters are set up in step 921, and the detectors are configured in a 180 degree orientation in step 922. Next, after configuring the detectors for coincidence mode acquisition in step 923, emission data is acquired for the complete range of projection angles, rotating the detectors between angular stops about the z axis as required (steps 924, 925 and 926). After the emission data is acquired, the detectors are reconfigured for singles-mode acquisition in step 927, and transmission data is acquired for the complete range of projection angles, rotating the detectors between angular stops about the z axis as required (steps 928, 929 and 930). An emission image is then reconstructed and corrected for attenuation using the transmission image data in step 931.

Correction of Emission Contamination in the Transmission Scan

If the transmission scan is performed after injection of the radionuclide into the patient, emission activity will be present during the transmission scan.

Figure 11A:
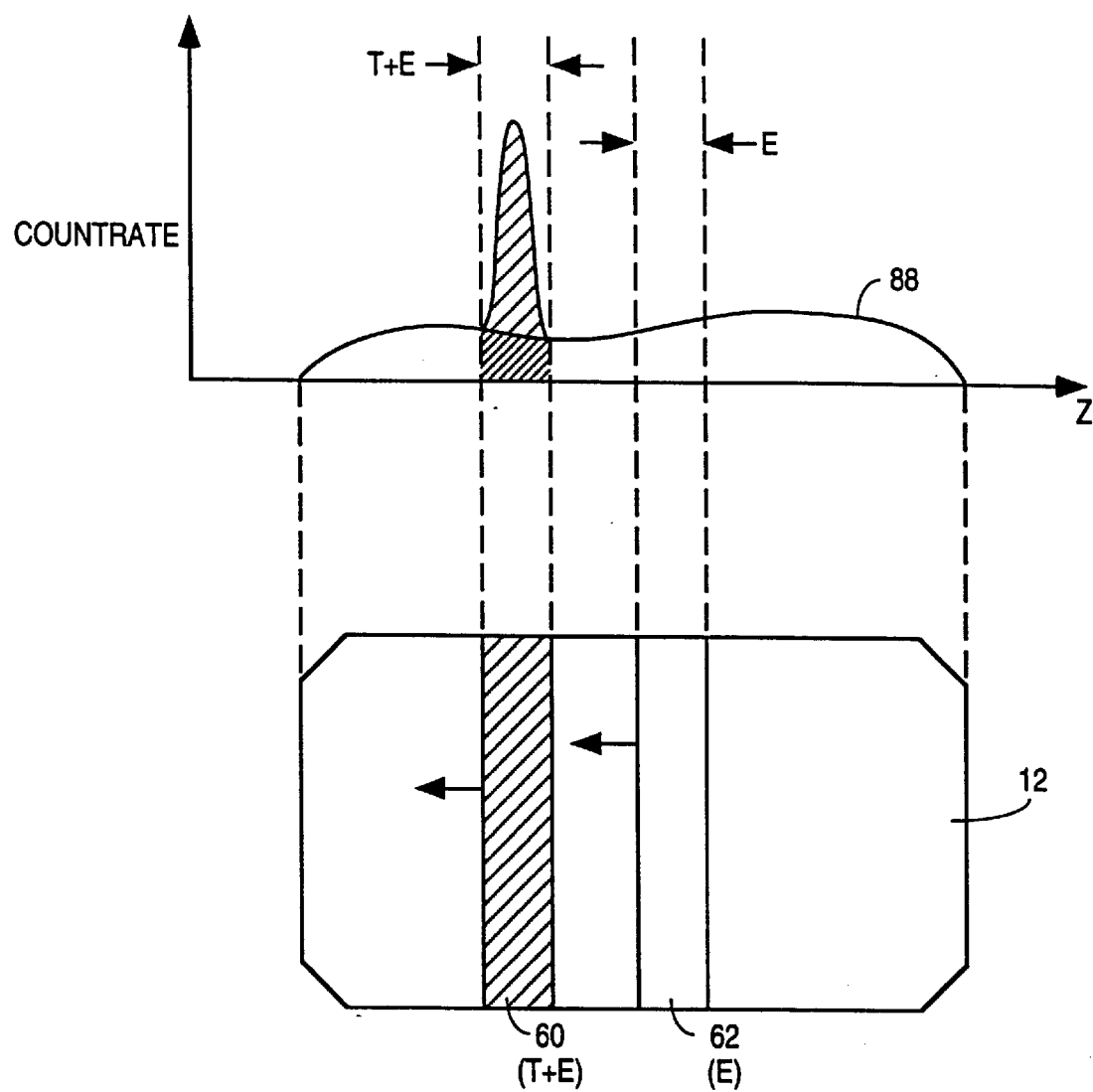
FIG. 11A illustrates countrate as function of position along the detector imaging surface and the spatial windowing for transmission (T+E) and contamination (F) events.
Figure 11B:
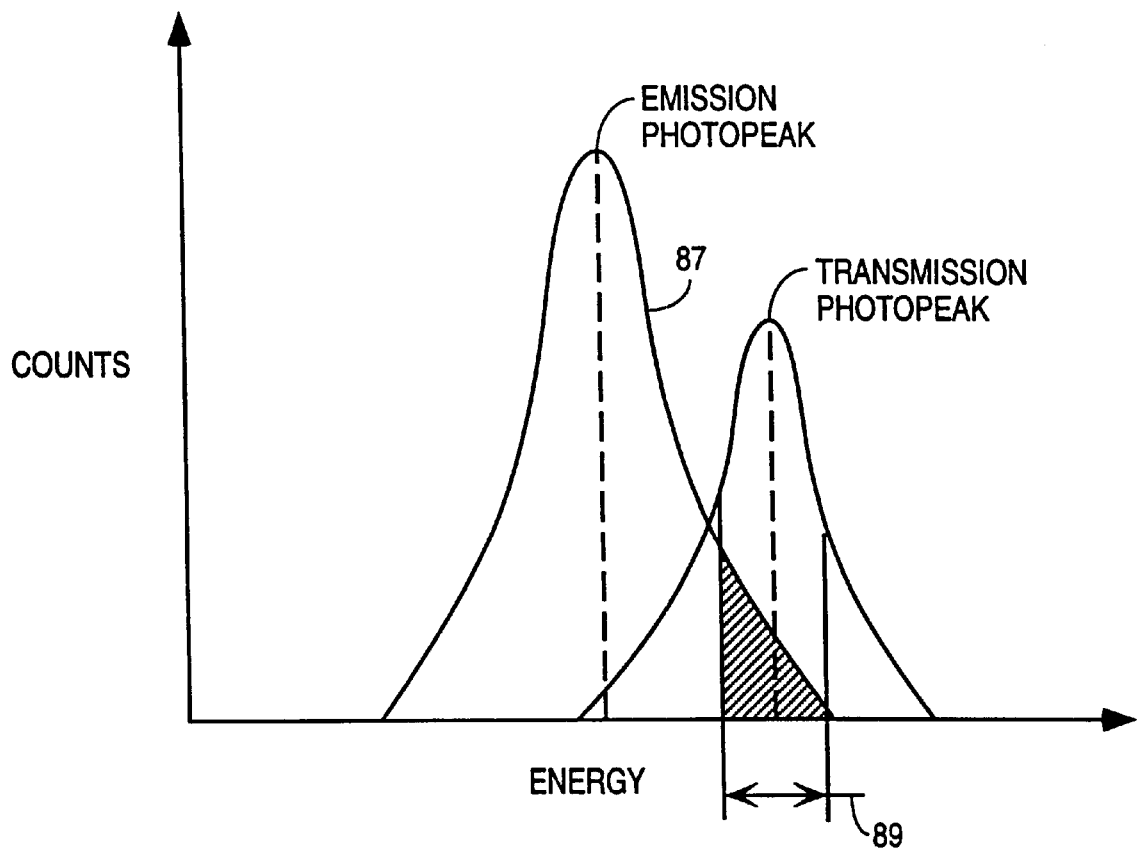
FIG. 11B illustrates a relationship between emission and transmission photopeaks for one embodiment.

Accordingly, some of the emission activity may be detected (undesirably) within transmission detection windows 60 and 61 (see FIGS. 5A and 5B). The effect of this emission contamination in the transmission detection scan is illustrated in FIG. 11A, which plots countrate as a function of axial (z) position along the imaging surface 12 of a detector. A baseline countrate 88 of emission activity exists across the entire imaging surface 12 of the detector. In addition, within the transmission detection window 60, there is additional countrate attributable to transmission radiation from the corresponding transmission source 31A (not shown in FIG. 11A). Energy discrimination as a means for distinguishing between emission activity and transmission activity becomes relatively ineffective if the emission source and transmission source have photopeaks that are close together (e.g., a $Cs^{137}$ singles transmission source with a photopeak at 662 keV and a Flouro Deoxy Glucose, or FDG, coincidence emission source with a photopeak at 511 keV). The reason energy discrimination becomes relatively ineffective is that, as illustrated in FIG. 11B, a portion of the emission energy distribution 87 will fall into the transmission energy acceptance range 89. Note that the energy acceptance range is not to be confused with transmission detection windows 60 and 61, which are spatial windows. As a result, some of the emission activity impinging on the transmission detection windows 60 and 61 will be incorrectly detected as transmission activity, thereby introducing inaccuracy into the transmission image.

Consequently, the present invention includes a technique for reducing emission contamination in the transmission scan. Specifically, emission contamination detection windows 62 and 63 are defined on the imaging surfaces 12 and 13 of detectors 10 and 11, respectively, for detection of photons in an energy acceptance range centered at the photopeak of the transmission source (i.e., 662 keV if a $Cs^{137}$ transmission source is used). That is, both the transmission detection windows 60 and 61 and the emission contamination detection windows 62 and 63 have energy acceptance ranges centered at the transmission photopeak, as shown in Figure 11B.

Figure 10:
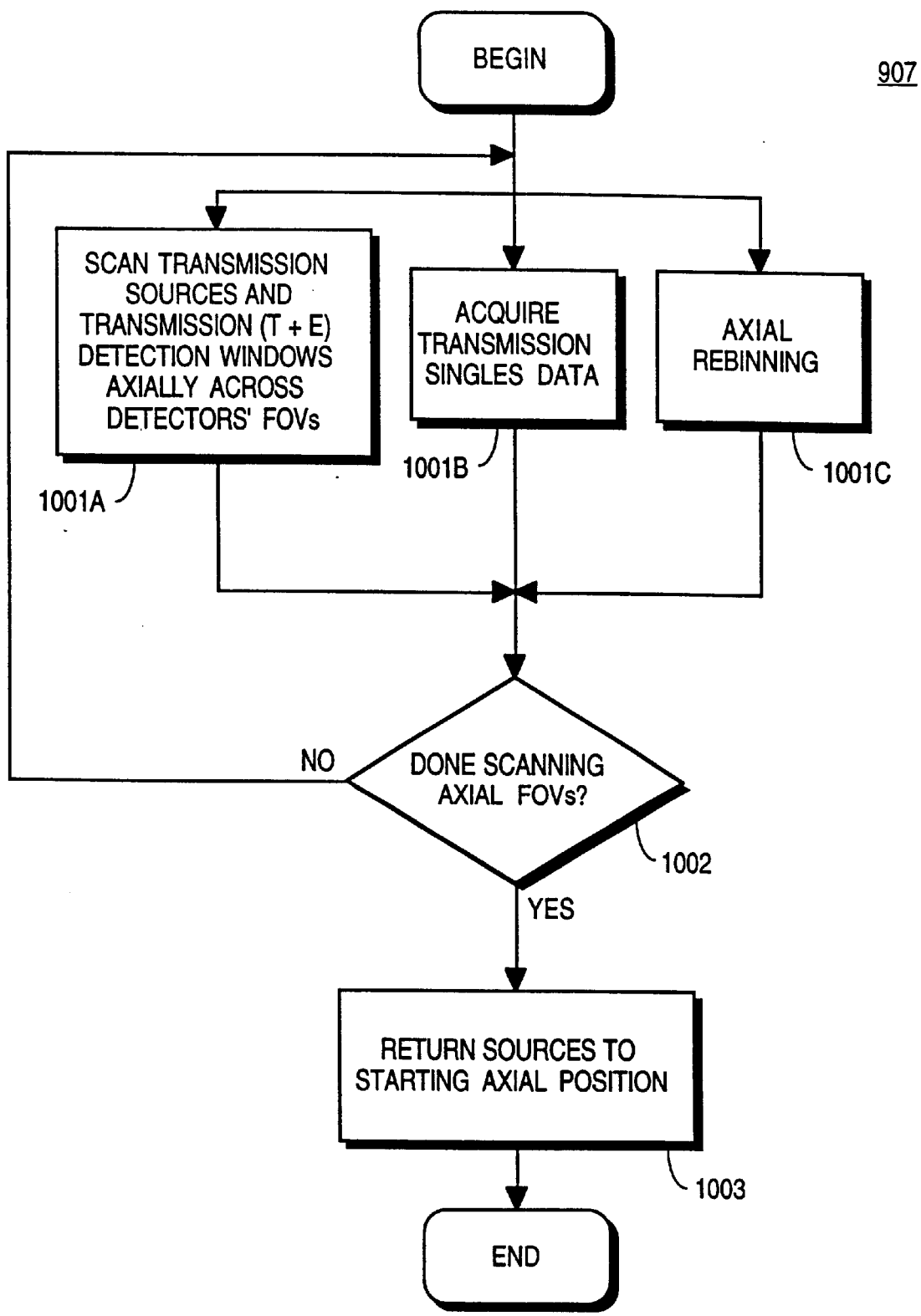
FIG. 10 is a flow diagram illustrating a routine for performing a transmission scan of an object.

Because the transmission detection windows 60 and 61 will receive some emission activity, those windows will henceforth be referred to in this description as the "T+E" (Transmission+Emission) windows 60 and 61 to facilitate description. Similarly, the emission contamination detection windows 62 and 63 (see FIGS. 5A, 5B, and 11) will henceforth be referred to as the "E" windows. Note that the emission singles rate falling within the transmission energy acceptance window does not change substantially over the short acquisition time period, regardless of whether the transmission beam is over the T+E window 60. Therefore, the emission count detected within the E window 62 can be used to subtract out the emission contamination within the T+E window 60. FIG. 10 illustrates in greater detail the step 907 (FIG. 9A) or 929 (FIG. 9B) of acquiring transmission data according to the above-mentioned technique.

At each angular stop, the transmission scan is characterized by three concurrent steps, 1001A, 1001B, and 1001C. In step 1001A, the transmission sources and the T+E detection windows 60 and 61 are scanned axially across the FOVs of the detectors 10 and 11, respectively. As the T+E windows 60 and 61 are scanned, transmission data is acquired in step 1001B based on radiation detected within the T+E windows 60 and 61 and rebinned into sinograms using an axial rebinning algorithm in step 1001C. This process repeats until the entire axial FOVs of detectors 10 and 11 have been scanned (step 1002), at which time the source assemblies 30 and 31 are returned to their initial axial positions in step 1003. Alternatively, after step 1002 the source assemblies 30 and 31 can be left at their final axial position and then scanned in the opposite direction axially for the next angular position of the detectors 10 and 11.

The present invention provides for correction of emission contamination in the transmission scan by measuring the emission countrate at various positions and points in time and correcting for emission contamination in real-time (i.e., on-the-fly, or as the events are detected) during the transmission scan and on an event-by-event basis, as will be described in greater detail below. In this context, correction "in real-time", "on-the-fly", or "as the events are detected" refers to when corrections are applied; specifically, it means that corrections are applied during the data acquisition process, as opposed to during post-processing. In contrast, correction on an "event-by-event basis" refers to how corrections are applied; specifically, it means that corrections are applied in response to individual detected events, as opposed to groups of events or complete images. Embodiments described below apply correction for emission contamination both in real-time and on an event-by-event basis. However, it is also contemplated that variations of these embodiments can be used to apply emission contamination corrections in real-time but not on an event-by-event basis, or to apply such corrections on an event-by-event basis but not in real-time. For example, correction can be applied during data acquisition (as opposed to post-processing after all data has been acquired) to groups of events rather than to individual events; in that case, the correction is performed "in real-time" but not on an "event-by-event basis" (i.e., on grouped data or on a complete image). In another example, individual events can be stored, such that correction is applied based on each individual stored event by post-processing after all data has been acquired (i.e., based on list mode data). In that case, the correction is done on an "event-by-event basis" but not "in real-time". In yet another example, grouped event data can be stored, such that correction is applied to groups of events during post-processing.

The correction technique includes defining the E windows 62 and 63 on the imaging surfaces 12 and 13 of detectors 10 and 11, respectively. The E windows 62 and 63 are scanned in synchronization with, but are offset axially from, the transmission T+E windows 60 and 61. For a given axial position of the E windows 62 and 63, the number of counts detected in the E windows 62 and 63 provides a good approximation of the emission activity impinging on the T+E windows 60 and 61 when the T+E windows 60 and 61 are located at the same position. Consequently, in accordance with one embodiment of the present invention, each time a count is detected in an E window of a detector, a count is removed from the corresponding location in a transmission projection buffer representing the data acquired in the T+E windows 60 and 61. The result is to effectively remove virtually all of the emission contamination from the transmission image.

Note that the fanbeam collimation of the point sources 30A and 31A enables this technique to be performed in conjunction with a singles transmission source. More specifically, the fanbeam collimation enables the simultaneous acquisition of both emission and singles transmission data with the same detector and in real-time, event-by-event correction. This technique is in contrast with prior techniques which make use of uncollimated coincidence sources and/or do not perform real-time or event-by-event correction of emission contamination. See, e.g., R. J. Smith et al., "Simultaneous Post Injection Transmission and Emission Contamination Scans in a Volume Imaging PET scanner," 1995 IEEE Nuclear Science Symposium and Medical Imaging Conference Record, Vol. 3, pages 1781–85, 1995, and R. J. Smith et al., "Post Injection Transmission Scanning in a Volume Imaging PET Camera," IEEE Transactions on Nuclear Science, vol. 41, No. 4, August 1994.

Figure 12A:
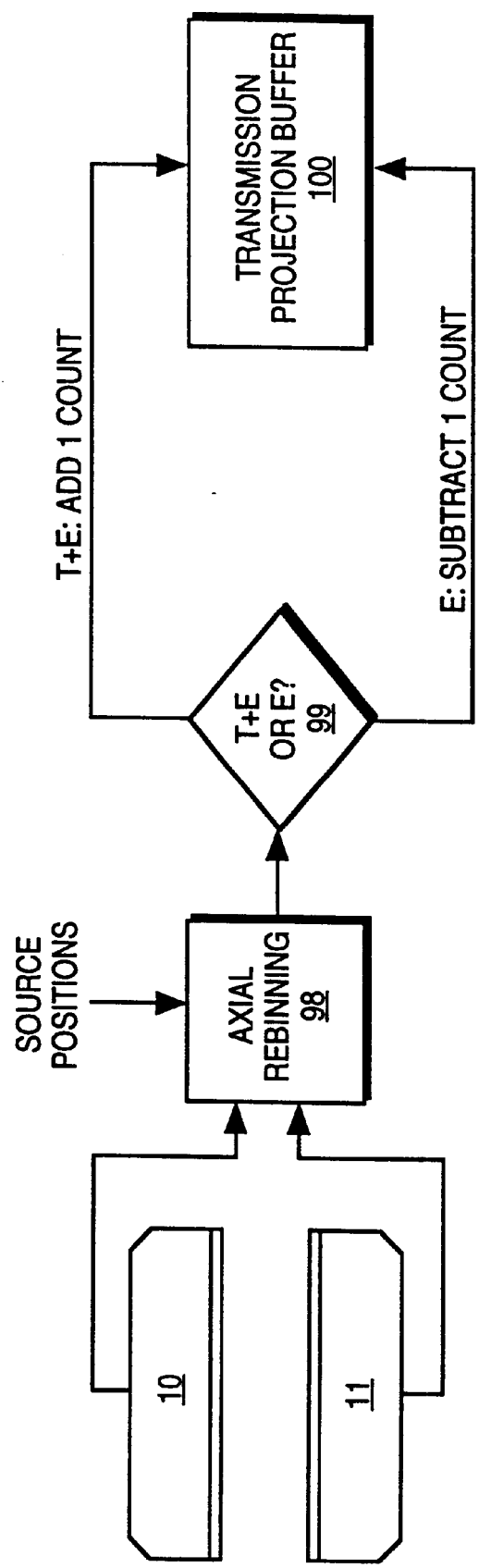
FIG. 12A is a block diagram illustrating a technique for correcting for emission contamination in a transmission image.

FIG. 12A further illustrates the above-described technique for correcting for emission contamination in the transmission scan. Transmission and emission radiation is detected by the detectors 10 and 11 using the scanning T+E and E detection windows, as described above. Information on the detected events (i.e., X and Y position and energy level Z) is provided to an axial rebinning algorithm 98, which receives as input the axial (z) positions of the sources 30A and 31A and the angular positions of the detectors and sources about the z axis. For each count detected in either the T+E window or the E window of one of the detectors 10 and 11, if the count was detected in an T+E window (block 99), then one count is added to the corresponding location in the transmission projection buffer 100, and if the count was detected within an E window, then one count is subtracted from the corresponding location in the transmission projection buffer 100. The counts subtracted from the transmission projection buffer 100 will substantially equate to the emission contamination counts undesirably added to the corresponding locations in the projection buffer 100. Note that the inputting of the source positions to axial rebinning algorithm 98 allows counts to be added or subtracted from the proper locations of the transmission projection buffer 100, such that correction of emission contamination can be performed in real-time and on an event-by-event basis and in a spatially dependent manner.

Figure 12B:
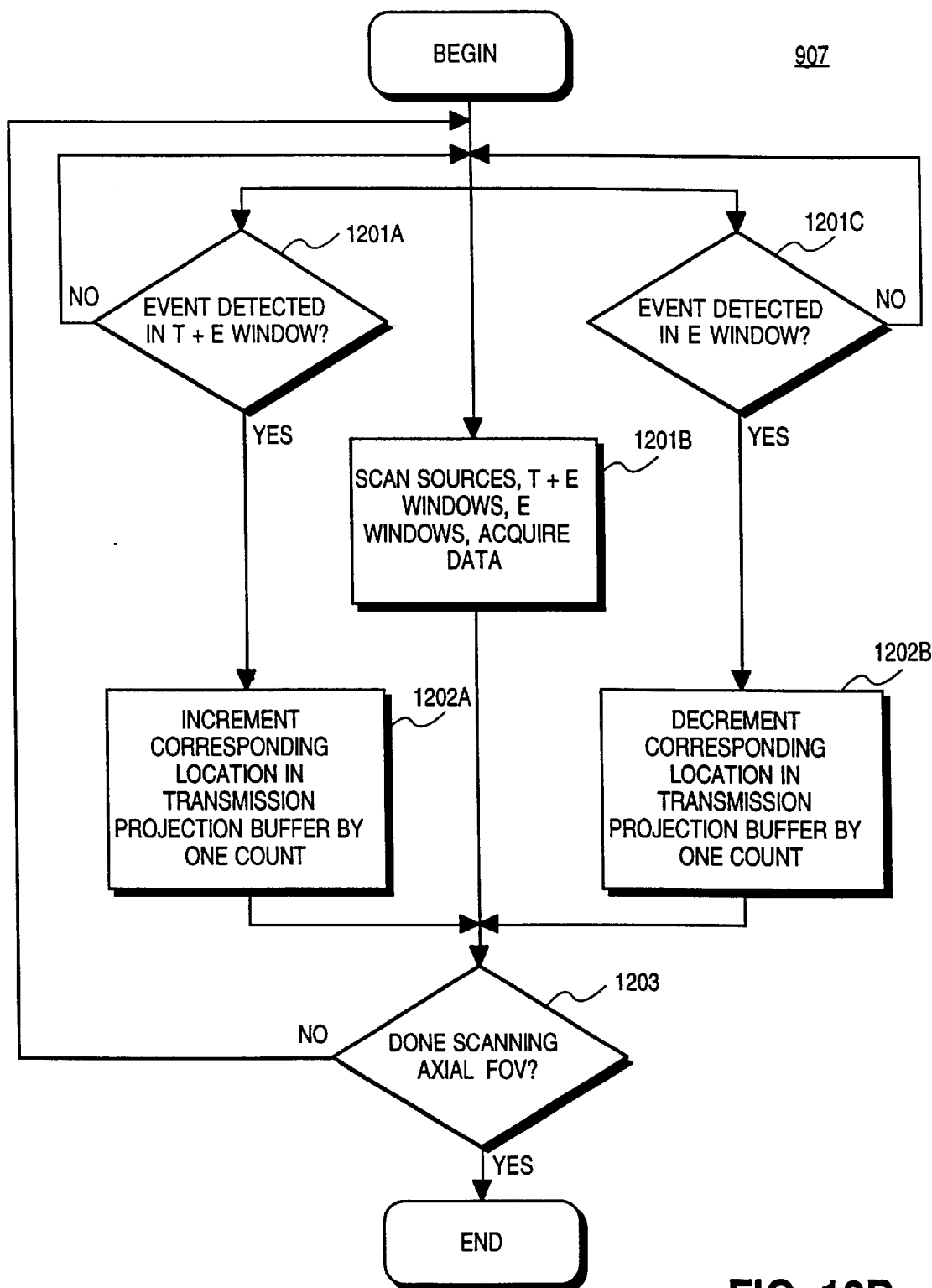
FIG. 12B is a flow diagram illustrating a routine for performing real-time correction of emission contamination during a transmission scan.

FIG. 12B illustrates the step 907 (or 929) of performing the transmission scan according to an embodiment which uses emission contamination correction in accordance with FIG. 12A. The routine is characterized by three concurrent processing paths. In the first path, it is determined in step 1201A whether an event has been detected in a T+E window. If so, the corresponding location in the transmission projection buffer 100 is incremented by one count in step 1202A; if not, the processing path repeats from the beginning. In the second processing path, the transmission sources, T+E windows, and E windows are scanned axially across the FOVs of their respective detectors to acquire data in step 1201B. In the third processing path, it is determined in step 1201C whether an event has been detected in an E window. If so, the corresponding location in the transmission projection buffer 100 is decremented by one count in step 1202B; if not, the processing path repeats from the beginning. After performing either step 1202A, 1201B, or 1202B, then if the entire axial FOV has not been scanned, then the routine repeats from the beginning; otherwise, the routine ends.

Note that the width of the T+E and E windows can be varied based on axial position to achieve the best windowing effect, such as when a window reaches the edge of the imaging surface. However, for any given axial position, the width of the T+E and E windows remains constant to ensure accurate correction.

As noted above, event data can be saved in list mode, such that it can be corrected event-by-event during post-processing. As an alternative, correction can be applied during data acquisition to groups of events.

Deadtime Correction

Figure 13:
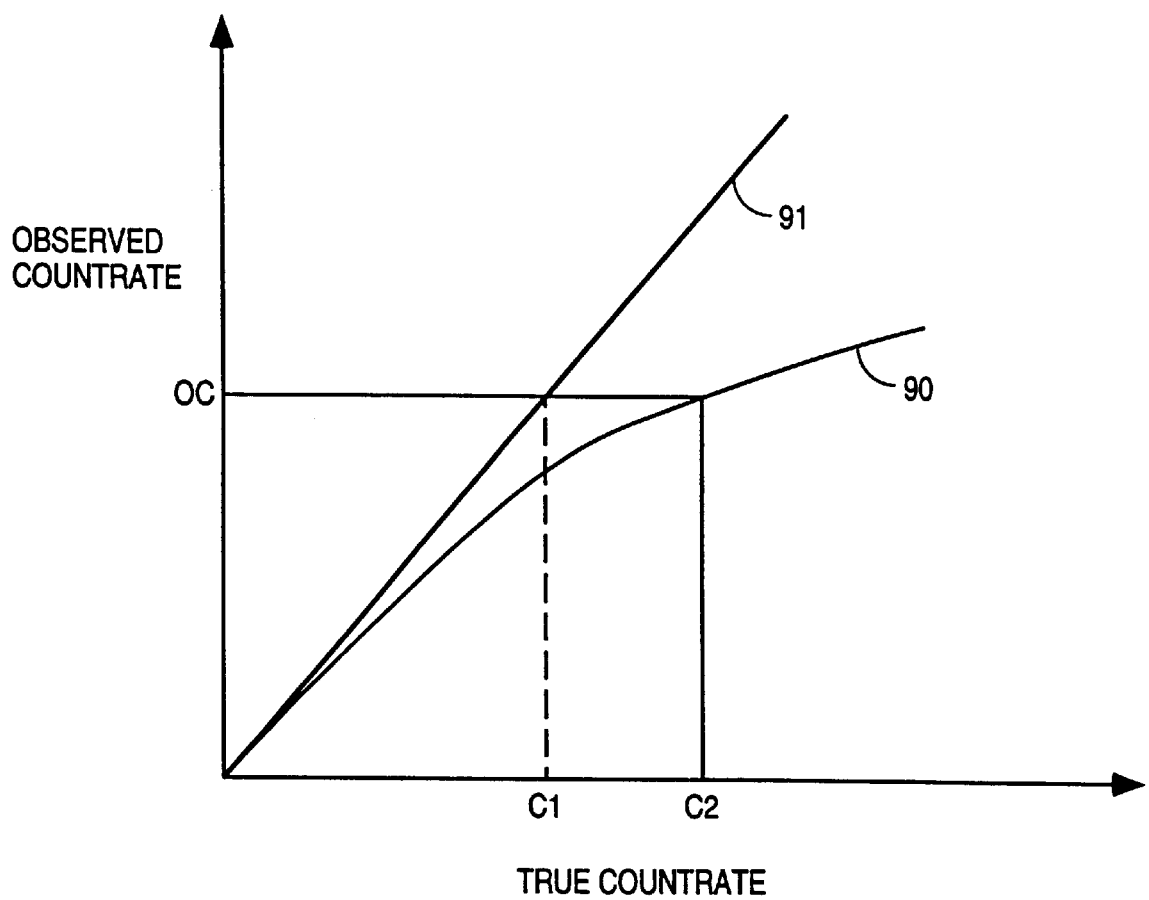
FIG. 13 is a graph illustrating effects of deadtime losses.

One problem associated with conventional gamma cameras is deadtime loss. Deadtime refers to the inability of a scintillation detector to distinguish two distinct scintillation events which occur very close together in time. Deadtime loss can be defined as the difference between the true countrate and the observed countrate which results from detector deadtime. FIG. 13 illustrates the effect of deadtime losses in the form of a plot of observed countrate against true countrate. Line 91 represents the ideal (but unrealistic) case in which there is no deadtime loss; in that case, the observed countrate OC equals the true countrate C1. In contrast, line 90 represents the response of a gamma camera system that is subject to deadtime loss; in that case, the observed countrate OC is lower than the true countrate C2. Note that the deadtime loss is dependent upon the singles rate; that is, as the singles rate (true countrate) increases the deadtime loss (difference between the true countrate and the observed countrate) also increases.

One technique for correcting for deadtime loss is to apply a single, global correction factor, which is not applied until after the data has been acquired. See, e.g., R. J. Smith et al., "Simultaneous Post Injection Transmission and Emission Contamination Scans in a Volume Imaging PET scanner," 1995 IEEE Nuclear Science Symposium and Medical Imaging Conference Record, vol. 3, pages 1781–85, 1995. However, the use of a global correction factor does not account for the spatial dependency of deadtime losses. In particular, deadtime loss is dependent upon the singles rate, which is dependent upon both axial position and projection angle. Therefore, the use of a global deadtime correction factor may introduce inaccuracies into the transmission image.

Hence, the present invention includes a technique for correcting for deadtime losses in the transmission data, the emission data, or both, taking into account the spatial dependency of the deadtime losses. The deadtime corrections can be applied in real-time or as post-processing, and in either case, they can be applied on an event-by-event basis or to groups of events. Because deadtime is dependent upon the singles rate, a singles rate vs. deadtime calibration curve can be derived for a given gamma camera system. Hence, in accordance with the present invention, a deadtime vs. singles rate calibration curve is empirically derived for the gamma camera system 1 and then used to create a look-up table of deadtime correction factors for various different singles rates. In one embodiment, each correction factor in the look-up table is a factor by which an observed count is multiplied during an imaging session before being added to the projection data (transmission or emission), in order to compensate for deadtime losses. Higher singles rates will correspond to higher deadtime losses and, therefore, higher correction factors from the look-up table. The look-up table can be an integer map, which may be created to have a number of entries chosen so as not to compromise the speed of rebinning.

As an example of this technique, if the current singles rate corresponds to no significant deadtime loss, then the corresponding location in the projection buffer can be increased by 50 counts, rather than one count, for each detected count. On the other hand, if there is a singles rate corresponding to a 2% deadtime loss, then the corresponding location in the projection buffer can be increased by 51 counts rather than one count. Note that increasing the number of counts in this way introduces an artificial magnification factor in the projection. The above example would introduce a magnification factor of 50 into the projection. This magnification can be removed during reconstruction, however, by scaling down the image accordingly at that time. It should be noted that the accuracy of the deadtime correction depends upon the magnification factor selected, the accuracy of the initial calibration, and (as applied to the transmission scan) the assumption that there is little or no variance of deadtime within the transmission beam.

Figure 14A:
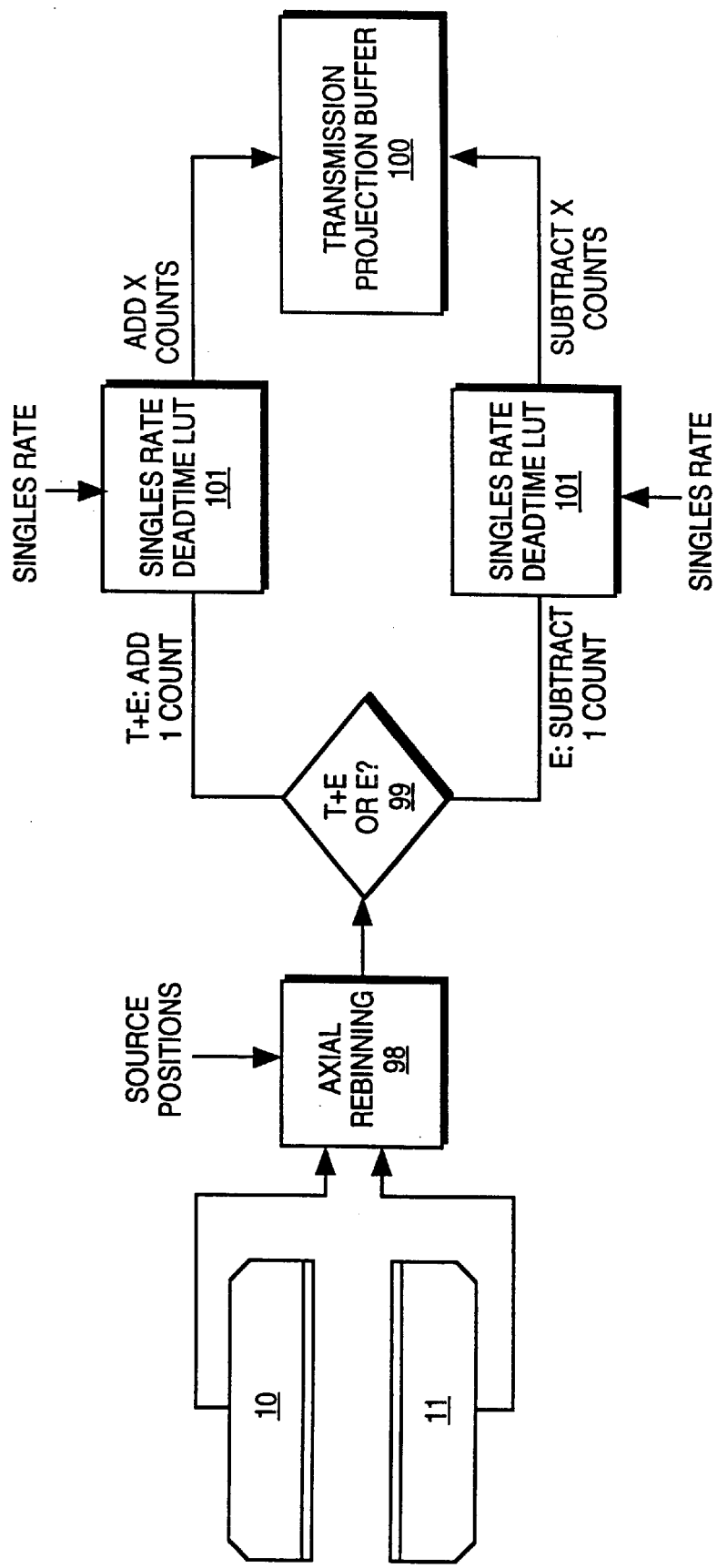
FIG. 14A is a block diagram illustrating a technique for performing real-time correction of transmission data for emission contamination and deadtime.

FIG. 14A illustrates a technique for implementing real-time, event-by-event deadtime correction of transmission data, as described above. In the illustrated embodiment, this technique is implemented in conjunction with the emission contamination correction technique described above. Specifically, the process flow of FIG. 14A is essentially the same as that of FIG. 12A with the exception of the addition of the singles rate deadtime look-up tables (LUTs) 101. If a count is detected in a T+E window (block 99), then rather than adding one count to the appropriate location in the transmission projection buffer 100, as in the case of FIG. 12A, X counts are added to that location in the buffer, where X is determined from the singles rate deadtime look-up table 101 based on the current singles rate. Similarly, if an event is detected in the E window, then rather than subtracting a single count from the appropriate location in the transmission projection buffer, X counts are subtracted from that location, where X is determined from the singles rate deadtime look-up table 101 based on the current singles rate. Note that, in one embodiment, the singles rate used for this purpose is the global singles rate (i.e., the singles rate observed across an entire detector) rather than the singles rate within either a T+E window or an E window.

As with correction of emission contamination, the correction for deadtime loss is performed in real-time and on an event-by-event basis. Accordingly, the source position (angular position about the z axis and axial position) is input to the axial rebinning algorithm 98 to enable each event to be associated with the appropriate location in the transmission projection buffer 100. This technique is in contrast with the above-mentioned technique in which a single, global correction factor is applied, which does not take into account the spatial dependency of deadtime losses. Note, however, that as with the emission contamination correction described above, it is also contemplated that variations of the described technique might be used to apply deadtime correction in real-time but not on an event-by-event basis, or on an event-by-event basis but not in real-time. For example, deadtime corrections can be applied to data stored in list mode during post-processing on an event-by-event basis. Alternatively, deadtime corrections can be applied to groups of events during the data acquisition process. Corrections can also be applied to grouped data during post-processing.

Figure 14B:
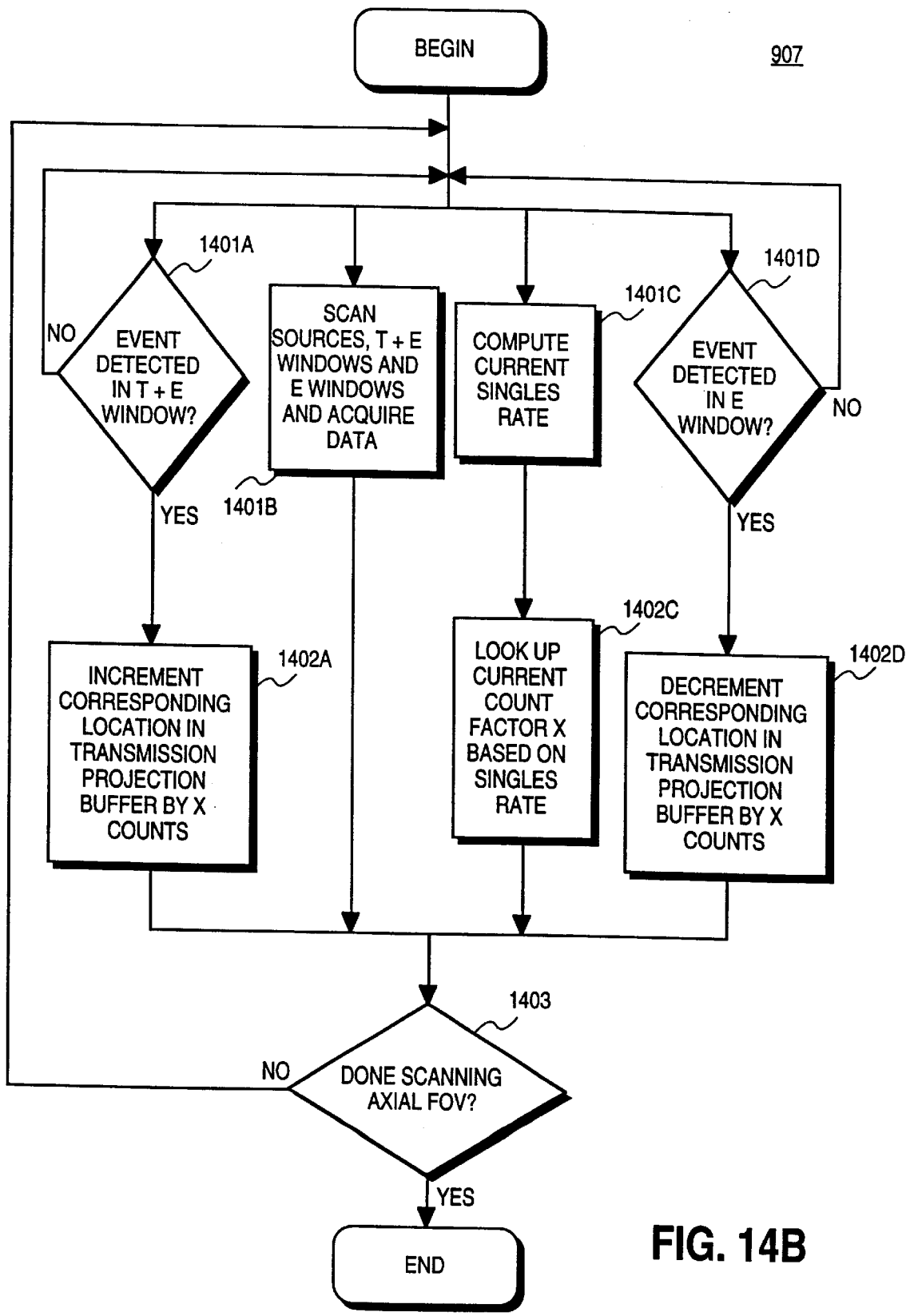
FIG. 14B is a flow diagram illustrating a routine for performing real-time correction for emission contamination and deadtime during a transmission scan.

FIG. 14B illustrates the step 907 (or 929) of performing the transmission scan according to an embodiment which uses in real-time, event-by-event correction of both deadtime loss and emission contamination, as described above. The routine is characterized by four concurrent processing paths. In the first processing path, it is determined in step 1401A whether an event has been detected in a T+E window; if not, the processing path repeats from the beginning. If an event has been detected in the T+E window, then in step 1402A, the corresponding location in the transmission projection buffer 100 is incremented by X counts, where X is determined in another concurrent processing path, as will be described below. A second processing path consists of step 1401B, in which the transmission sources 30A and 31A, the T+E windows 60 and 61, and the E windows 62 and 63 are scanned axially to acquire data. A third processing path begins with step 1401D, in which it is determined whether an event has been detected in an E window; if not, the processing path repeats from the beginning. If an event has been detected in the E window, then in step 1402D the corresponding location in the transmission projection buffer 100 is decremented by X counts, where X is determined in the fourth concurrent processing path as follows. In the fourth concurrent processing path, the current singles rate is computed in step 1401C. As noted above, the singles rate in this embodiment is the global singles rate for the detectors 10 and 11 for this particular detector angle. Based on the current singles rate, the current count factor X is determined from the look-up table in step 1402C. After completion of any of the four concurrent processing paths, then the routine repeats from the beginning if the entire axial field of view has not yet been scanned (step 1403). Otherwise, the routine ends.

Figure 14C:
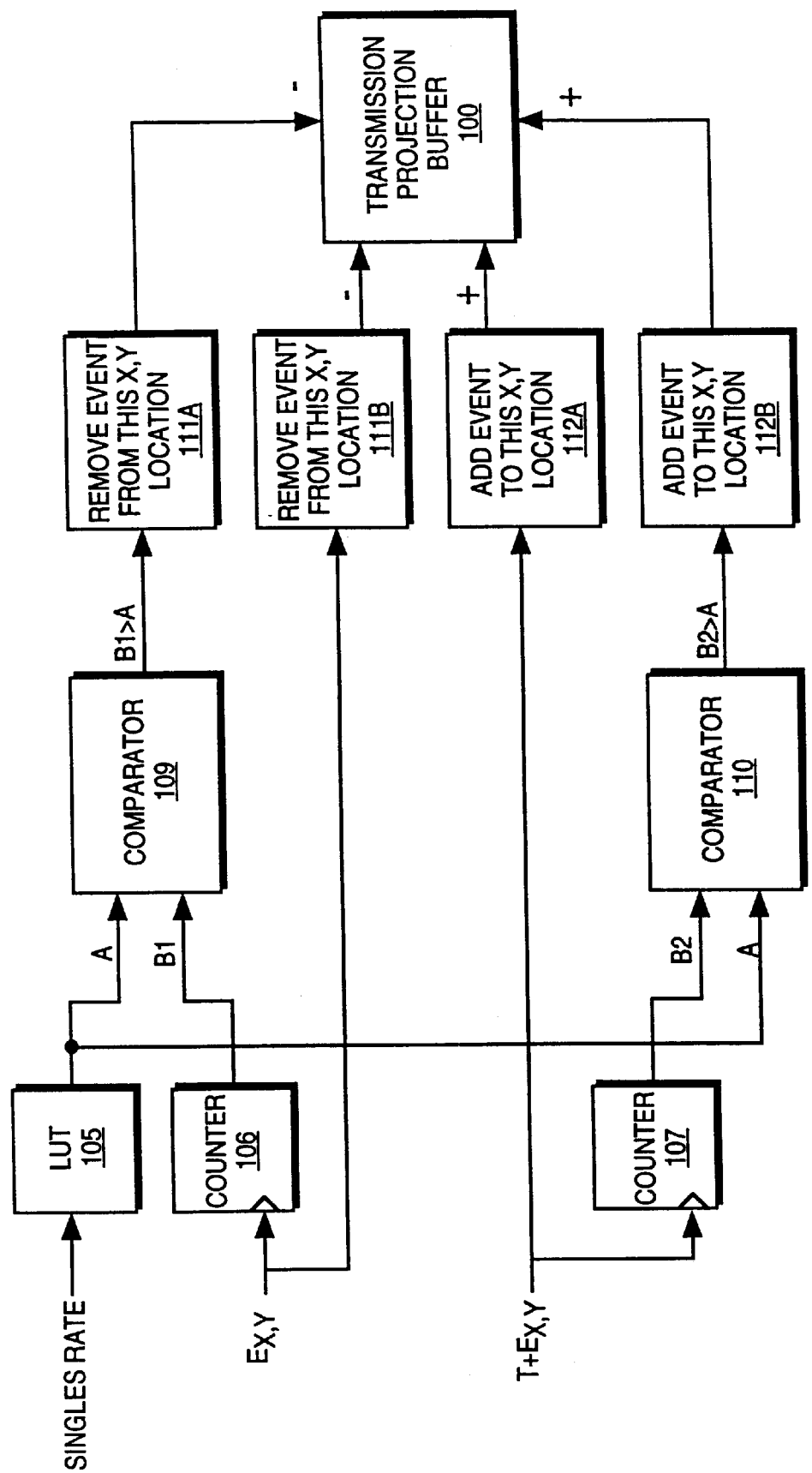
FIG. 14C is a block diagram illustrating an alternative technique for performing real-time correction of transmission data for emission contamination and deadtime.

FIG. 14C shows an alternative embodiment for implementing in real-time, event-by-event deadtime correction and emission contamination correction. Note that the embodiment of FIG. 14C, as with other aspects of the present invention, can be implemented in software, hardware, or a combination thereof. In contrast with the embodiment of FIGS. 14A and 14B, each observed count is not multiplied by a factor in the embodiment of FIG. 14C. Rather, each count generally is represented as one count in the transmission projection buffer 100. However, additional counts may be added or subtracted to appropriate locations of the transmission projection buffer 100 depending upon the observed singles rate at a given point in time and the spatial window (T+E or E) in which a given count is detected.

The technique of FIG. 14C includes a look-up table 105, which outputs a value A that is based on the current singles rate. The technique also includes counters 106 and 107, each of which counts up in response to its clock input to a maximum value MAXCOUNT and then automatically resets to zero. Counter 106 is clocked by signal $E_{x,y}$, which is asserted each time an event is detected in the E window. Counter 106 outputs a signal B1. Similarly, counter 107 receives a signal $T+E_{x,y}$ at its clock input, which is asserted each time an event is detected in the T+E window, and outputs a signal B2.

The technique of FIG. 14C also includes two comparators 109 and 110. Comparator 109 receives as input signals A and B1 and asserts its output signal when B1 is greater than A (i.e., when the output of counter 106 exceeds the output of look-up table 105). Comparator 110 receives as input signals A and B2, and asserts its output when B2 is greater than A (i.e., when the output of counter 107 exceeds the output of look-up table 105).

Look-up table 105 is generated in a manner similar to that described above in connection with FIGS. 14A and 14B. That is, look-up table 105 is created based on empirical data and provides output signal A having a value based on the global input singles countrate. Specifically, the value A output by look-up table 105 is based on the following equation:

$$A = MAXCOUNT * (COUNTRATE_{observed} + (COUNTRATE_{true} - COUNTRATE_{observed})/2)$$

where:
$COUNTRATE_{true}$ is the true countrate if the deadtime were zero,
$COUNTRATE_{observed}$ is the intrinsic observed countrate, and
MAXCOUNT is the maximum value of the free running counters 106 and 107.

Each time an event is detected in the T+E window (i.e., each time $T+E_{x,y}$ is asserted), block 112A causes one event to be added to the appropriate x,y location of transmission projection buffer 100. In addition, if B2 is greater than A, block 112B causes an additional event to be added to the appropriate x,y location of transmission projection buffer 100 in response to assertion of signal $T+E_{x,y}$. Adding such additional events compensates for deadtime losses. However, events must also be removed from transmission projection buffer 100 to correct for emission events detected in the T+E window. Accordingly, each time an event is detected in the E window (i.e., each time $E_{x,y}$ is asserted), block 111B causes one event to be subtracted from the corresponding location in the transmission projection buffer 100. In addition, if B1 is greater than A, block 111A causes an additional event to be subtracted from the corresponding x,y location in the transmission projection buffer 100 in response to assertion of signal $E_{x,y}$. Hence, the technique illustrated in FIG. 14C provides correction on an event-by-event basis of both deadtime losses and emission contamination in the transmission scan.

Note that the predetermined contents of the look-up table 105 as well as the value of MAXCOUNT will determine the actual response of the illustrated embodiment (i.e., how frequently additional events will be added or subtracted to/from the transmission projection for a given singles rate). As in the embodiments discussed above, this technique is advantageous in comparison to previous techniques which do correct for the spatial variances in deadtime or emission contamination.

FIG. 14D illustrates a technique similar to that in FIG. 14A, but for correcting emission data for deadtime. The axial rebinning module 102 rebins data acquired by detectors 10 and 11 during an emission scan. The deadtime LUT 103 adds an appropriate number of counts to the emission projection buffer 104 based on the current singles rate. As with the above-described techniques, variations of this technique might be used to apply deadtime correction in real-time but not on an event-by-event basis, or on an event-by-event basis but not in real-time.

Thus, a method and apparatus for correcting for emission contamination and deadtime loss in a nuclear medicine imaging system have been described. Although the present invention has been described with reference to specific exemplary embodiments, it will be evident that various modifications and changes may be made to these embodiments without departing from the broader spirit and scope of the invention as set forth in the claims. Accordingly, the specification and drawings are to be regarded in an illustrative rather than a restrictive sense.

What is claimed is:

1. A medical imaging system comprising:
   means for detecting radiation-induced events to generate data of an object;
   means for correcting the data of the object for emission contamination on an event-by-event basis; and
   means for generating an image of the object based on the corrected data.

2. A medical imaging system according to claim 1, wherein the means for correcting comprises means for correcting the data for emission contamination on an event-by-event basis in real-time.

3. A medical imaging system according to claim 1, wherein the means for correcting comprises means for correcting the data for emission contamination on an event-by-event basis during post-processing.

4. A medical imaging system according to claim 1, further comprising means for correcting the data for deadtime on an event-by event basis.

5. A medical imaging system according to claim 4, wherein the means for correcting the data for deadtime comprises means for correcting the data for deadtime on an event-by event basis in real-time.

6. A medical imaging system comprising:
   means for detecting radiation-induced events to generate data of an object;
   means for correcting the data of the object for deadtime on an event-by-event basis; and
   means for generating an image of the object based on the corrected data.

7. A medical imaging system according to claim 6, wherein the means for correcting comprises means for correcting the data for deadtime on an event-by-event basis in real-time.

8. A medical imaging system according to claim 6, wherein the means for correcting comprises means for correcting the data for deadtime on an event-by-event basis during post-processing.

9. A medical imaging system according to claim 8, further comprising means for correcting the data for emission contamination on an event-by event basis.

10. A medical imaging system according to claim 9, wherein the means for correcting the data for emission contamination comprises means for correcting the data for emission contamination on an event-by event basis in real-time.

11. A medical imaging system according to claim 6, wherein the means for detecting comprises means for detecting the radiation-induced events from a plurality of angles, and wherein the means for correcting comprises means for correcting the data for deadtime on an event-by event basis, based on an event rate for each of the angles.

12. In a nuclear medicine imaging system, a method of generating images of an object, the method comprising:
   detecting radiation-induced events;
   generating data of the object based on the detected events;
   correcting the data for emission contamination on an event-by-event basis; and
   generating images of the object based on the corrected data.

13. A method according to claim 12, wherein said correcting comprises correcting the data for emission contamination on an event-by-event basis in real-time.

14. A method according to claim 13, further comprising correcting the data for deadtime on an event-by event basis.

15. A method according to claim 13, further comprising correcting the data for deadtime on an event-by-event basis in real time.

16. A method according to claim 12, wherein said correcting comprises correcting the data for emission contamination on an event-by-event basis during post-processing.

17. In a medical imaging system, a method of generating images of an object, the method comprising:
   detecting radiation-induced events;
   generating data of the object based on the detected events;
   correcting the data for deadtime on an event-by-event basis; and
   generating images of the object based on the corrected data.

18. A method according to claim 17, wherein said correcting comprises correcting the data for deadtime on an event-by-event basis in real-time.

19. A method according to claim 17, wherein said correcting comprises correcting the data for deadtime on an event-by-event basis during post-processing.

20. A method according to claim 19, further comprising correcting the data for emission contamination on an event-by event basis.

21. A method according to claim 20, wherein said correcting the data for emission contamination comprises correcting the data for emission contamination on an event-by event basis in real-time.

22. A method according to claim 19, wherein said detecting comprises detecting the radiation-induced events from a plurality of angles, and wherein said correcting comprises correcting the data for deadtime on an event-by event basis based on an event rate for each of the angles.

23. A nuclear medicine imaging system comprising:
   means for detecting transmission radiation-induced events;
   means for generating transmission data of an object to be imaged based on the detected events;
   means for correcting the transmission data for emission contamination in real-time; and
   means for generating images of the object based on the corrected data.

24. A nuclear medicine imaging system according to claim 23, wherein said means for correcting the transmission data for emission contamination in real-time comprises means for correcting the transmission data for emission contamination on an event-by-event basis.

25. A nuclear medicine imaging system according to claim 24, further comprising means for correcting the transmission data for deadtime in real-time.

26. A nuclear medicine imaging system according to claim 25, wherein said means for correcting the transmission data for deadtime in real-time comprises means for correcting the transmission data for deadtime on an event-by-event basis.

27. A nuclear medicine imaging system according to claim 26, wherein said means for correcting the data for deadtime comprises means for correcting groups of events for deadtime in real-time.

28. A nuclear medicine imaging system according to claim 23, wherein said means for correcting the transmission data for emission contamination in real-time comprises means for correcting groups of events for emission contamination in real-time.

29. A nuclear medicine imaging system comprising:
means for detecting radiation-induced events;
means for generating data of an object to be imaged based on the detected events;
means for correcting the data for deadtime in real-time; and
means for generating images of the object based on the corrected data.

30. A nuclear medicine imaging system according to claim 29, wherein said means for correcting the data for deadtime in real-time comprises means for correcting transmission data for emission contamination on an event-by-event basis.

31. A nuclear medicine imaging system according to claim 29, wherein said means for detecting comprises means for detecting the radiation-induced events from each of a plurality of angles about the object, and wherein said means for correcting the data for deadtime in real-time comprises means for correcting the data for deadtime in real-time based on the angles at which said events are detected.

32. A nuclear medicine imaging system according to claim 31, wherein said means for correcting the data for deadtime in real-time comprises means for correcting the data for deadtime on an event-by-event basis.

33. A nuclear medicine imaging system according to claim 31, further comprising means for measuring a current singles rate at each of the plurality of angles;
wherein said means for correcting the data for deadtime based on the angles comprises means for correcting the data for deadtime based on the singles rate measured at each of the angles.

34. A nuclear medicine imaging system according to claim 33, wherein said means for correcting for deadtime based on the angles further comprises, means for populating an image projection by a number of counts based on the current singles rate for each detected event.

35. A method of generating images of an object in a medical imaging system, the method comprising:
detecting transmission radiation-induced events;
generating transmission data of the object based on the detected events;
correcting the transmission data for emission contamination in real-time; and
generating images of the object based on the corrected transmission data.

36. A method according to claim 35, wherein said correcting the transmission data for emission contamination in real-time comprises correcting the transmission data for emission contamination on an event-by-event basis.

37. A method according to claim 36, further comprising correcting the transmission data for deadtime in real-time.

38. A method according to claim 37, wherein said correcting the transmission data for deadtime in real-time comprises correcting the transmission data for deadtime on an event-by-event basis.

39. A method according to claim 35, wherein said correcting the transmission data for emission contamination in real-time comprises correcting groups of events for emission contamination in real-time.

40. A method of generating images of an object in a medical imaging system, the method comprising:
detecting radiation-induced events;
generating data of the object based on the detected events;
correcting the data for deadtime in real-time; and
generating images of the object based on the corrected data.

41. A method according to claim 40, wherein said correcting the data for deadtime in real-time comprises correcting transmission data for emission contamination on an event-by-event basis.

42. A method according to claim 41, wherein said detecting comprises detecting the radiation-induce events from each of a plurality of angles about the object, and wherein said correcting the data for deadtime in real-time comprises correcting the data for deadtime in real-time based on the angles at which said events are detected.

43. A method according to claim 43, wherein said correcting the data for deadtime in real-time comprises correcting the data for deadtime on an event-by-event basis.

44. A method according to claim 42, further comprising measuring a current singles rate at each of the plurality of angles;
wherein said correcting the data for deadtime based on the angles comprises correcting the data for deadtime based on the singles rate measured at each of the angles.

45. A method according to claim 44, wherein said correcting for deadtime based on the angles further comprises, for each detected event, populating an image projection by a number of counts based on the current singles rate.

46. A method according to claim 40, wherein said correcting the data for deadtime in real-time comprises correcting groups of events for emission contamination in real-time.

47. A method of generating images of an object in a medical imaging system, the method comprising:
detecting radiation-induced events;
generating data of the object based on the detected events;
correcting the data for both emission contamination and deadtime in real-time; and
generating images of the object based on the corrected data.

48. A method according to claim 47, wherein said correcting the data for both emission contamination and deadtime in real-time comprises correcting the data for both emission contamination and deadtime on an event-by-event basis.

49. A medical imaging system comprising:
a radiation source configured to transmit radiation through an object to be imaged;
a radiation detector configured to concurrently detect events induced by the transmitted radiation and events induced by emission radiation emitted from within the object, to acquire transmission data and emission data, respectively; and
a processing system configured to correct the transmission data for emission contamination in real-time based on the emission data and to generate images of the object based on the corrected data.

50. A medical imaging system according to claim 49, wherein the processing system is further configured to correct the transmission data for emission contamination on an event-by-event basis in real-time, based on the emission data.

51. A medical imaging system according to claim 50, wherein the processing system is further configured to correct the transmission data for deadtime in real-time.

52. A medical imaging system according to claim 49, wherein the processing system is further configured to correct groups of events for emission contamination in real-time, based on the emission data.

53. A medical imaging system according to claim 49, wherein the processing system is further configured to correct the transmission data for deadtime on an event-by-event basis in real-time.

54. A medical imaging system comprising:
   a radiation detector configured to detect radiation-induced events to acquire a set of data of an object to be imaged;
   a gantry movably supporting the detector; and
   a processing system configured to control the detector and the gantry and to correct the data for deadtime in real-time.

55. A medical imaging system according to claim 54, wherein the processing system is further configured to correct the data for deadtime on an event-by-event basis in real-time.

56. A medical imaging system according to claim 55, further comprising a radiation source configured to transmit radiation through the object to the detector, the detector further configured to detect radiation-induced events resulting from the transmitted radiation to acquire transmission data and radiation-induced events resulting from emission radiation to acquire a set of emission data, wherein the processing system is further configured to correct the transmission data for emission contamination in real-time.

57. A medical imaging system according to claim 54, wherein the processing system is further configured to correct groups of events for deadtime in real-time.

58. A medical imaging system according to claim 54, wherein the processing system is further configured to correct the transmission data for emission contamination on an event-by-event basis in real-time.

* * * * *